(12) United States Patent
Fritsch et al.

(10) Patent No.: US 7,645,615 B1
(45) Date of Patent: Jan. 12, 2010

(54) SELF-CONTAINED MICROELECTROCHEMICAL BIOASSAY PLATFORMS AND METHODS

(75) Inventors: Ingrid Fritsch, Fayetteville, AR (US); Robert Beitle, Jr., Fayetteville, AR (US); Zoraida Aguilar, Cincinnati, OH (US)

(73) Assignee: Board of Trustees of The University of Arkansas, N.A., Little Rock, AR (US)

( * ) Notice: Subject to any disclaimer, the term of this patent is extended or adjusted under 35 U.S.C. 154(b) by 0 days.

(21) Appl. No.: 12/054,229

(22) Filed: Mar. 24, 2008

Related U.S. Application Data

(62) Division of application No. 10/253,187, filed on Sep. 24, 2002, now Pat. No. 7,348,183.

(51) Int. Cl.
*G01N 33/543* (2006.01)
(52) U.S. Cl. .................................... 436/518
(58) Field of Classification Search ................ None
See application file for complete search history.

(56) References Cited

U.S. PATENT DOCUMENTS

| | | | | |
|---|---|---|---|---|
| 6,548,311 B1 * | 4/2003 | Knoll | ......... | 436/524 |
| 6,887,714 B2 | 5/2005 | Fritsch et al. | | |
| 7,348,183 B2 | 3/2008 | Fritsch et al. | | |

OTHER PUBLICATIONS

Sagar, S.L., Beitle, R.R., Ataai, M.M., Domach, M.M. Metal-Based Affinity Separation of α- and γ-Chymotrypsin. Bioseparations 3 (1992) 291.
Beitle, R.R., Ataai, M.M. Immobilized Metal Affinity Chromatography and Related Techniques. In New Developments in Bioseparation. AIChE Symposium #88 (1992).
Hoefling, T.A., Beitle, R.R., Enick, R.M., Beckman, E.J. Design and Synthesis of Highly CO2-Soluble Surfactants and Chelating Agents, Fluid Phase Equilibria 83 (1993) 203.
Ataai, M.M., Beitle, R.R. Use of Divalent Metal Ions Chelated to Sepharose and Agarose Derivitives for Reversible Protein Immobilization. In: Methods in Molecular Biotechnology: Immobilization of Enzymes and Cells #1 (1996).
Chai, S.A., Beitle, R.R., Coleman, M.R. Facilitated Transport Metal Affinity Membranes. Int. J. Biochromatography 2 (1996) 125.
Abudiab, T.A., Beitle, R.R. Preparation and Use of Magnetic Immobilized Metal Affininty Separation Media for Protein Isolation. J. Chromatography A 795 (1998) 211.
J. Crawford, S. Ramakrishnan, S. Gardner, M. Coleman, R. Beitle. Immobilized Metal Affinity Membrane Chromatography: Characteristics of Two Materials of Differing Preparation Chemistries. Separation Science and Technology 34 (1999) 2793.
Taylor, A., Oxford, C., Crookston, D., Beitle, R.R., Coleman, M.R. Effect of Chelated Metal on Amino Acid Transport in Facilitated Transport Membranes Incorporating Metal Affinity. In: ACS Symposium 744 on Membrane Formation and Modification (2000) 238.
Everett, W.R.; Welch, T.; Reed, L.; Fritsch-Faules, I. "Potential-Dependent Stability of Self-Assembled Organothiols on Gold Electrodes in Methylene Chloride", Anal. Chem. 1995, 34, 292-298.
Everett, W.R.; Fritsch-Faules, I. "Factors that Influence the Stability of Self-Assembled Organothiols on Gold under Electrochemical Conditions", Analytica Chimica Acta, 1995, 307, 253-268.
Scott, J.R.; Baker, L.; Everett, W.R.; Wilkins, C.L.; Fritsch, I. "Exchange Studies of Air Oxidized Alkanethiol Self-Assembled Monolayers on Gold", Anal. Chem., 1997, 69, 2636-2639.
Gong, W.; Elitzin, V. I.; Janardhanam, S.; Wilkins, C. L.; Fritsch, I., "Effect of Laser Fluence on Laser Desorption Mass Spectra of Organothiol Self-Assembled Monolayers on Gold", J. Am. Chem. Soc., 2001, 123, 769-770.
Aguilar, Z. P.; Vandaveer, W. R.; Fritsch, I., "Self-Contained Microelectrochemical Immunoassay for Small Volumes using Mouse IgG as a Model System", Anal. Chem. 2002, 74, 3321-3329.
Henry, C.S.; Fritsch, I. "Microfabricated Recessed Microdisk Electrodes: Characterization in Static and Convective Solutions", Anal. Chem., 1999, 71, 550-556.
Henry, C.S.; Fritsch, I. "Microcavities Containing Individually-Addressable Recessed Microdisk and Tubular Nanoband Electrodes", J. Electrochem. Soc., 1999, 146, 3367-3373.
Henry, C. S.; Vandaveer, IV, W. R.; Mubarak, I; Gray, S. R.; Fritsch, I. "Self-Contained Microelectrochemical Detectors for Analysis in Small Volumes of Static and Flowing Fluids", in Micro Total Analysis Systems 2001, J. Michael Ramsey and Albert van den Berg (Eds.), Kluwer Academic Publishers: Monterey, CA, 2001, pp. 321-322.

\* cited by examiner

*Primary Examiner*—Ann Y Lam
(74) *Attorney, Agent, or Firm*—Head, Johnson & Kachigian, P.C.

(57) ABSTRACT

Methods and devices for improved chemical and biological detection assays combined well defined microstructures having independently addressable electrodes with various surface immobilization electrochemical assays. Combining known chemical detection immobilization assays, electrochemically active moieties with microstructures having independently addressable electrodes provides for vastly improved methods of detecting microorganisms, chemical compounds, and measuring membrane transport.

21 Claims, 11 Drawing Sheets

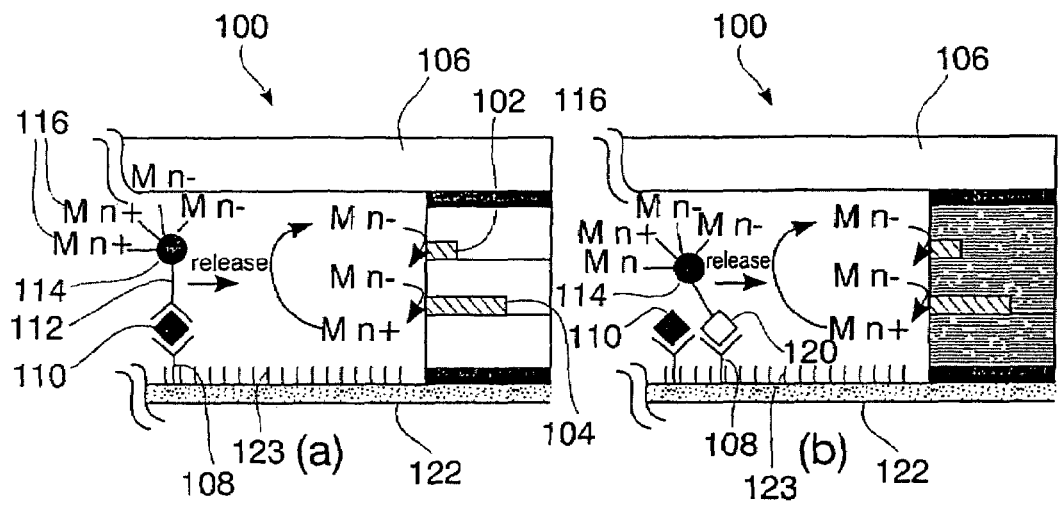
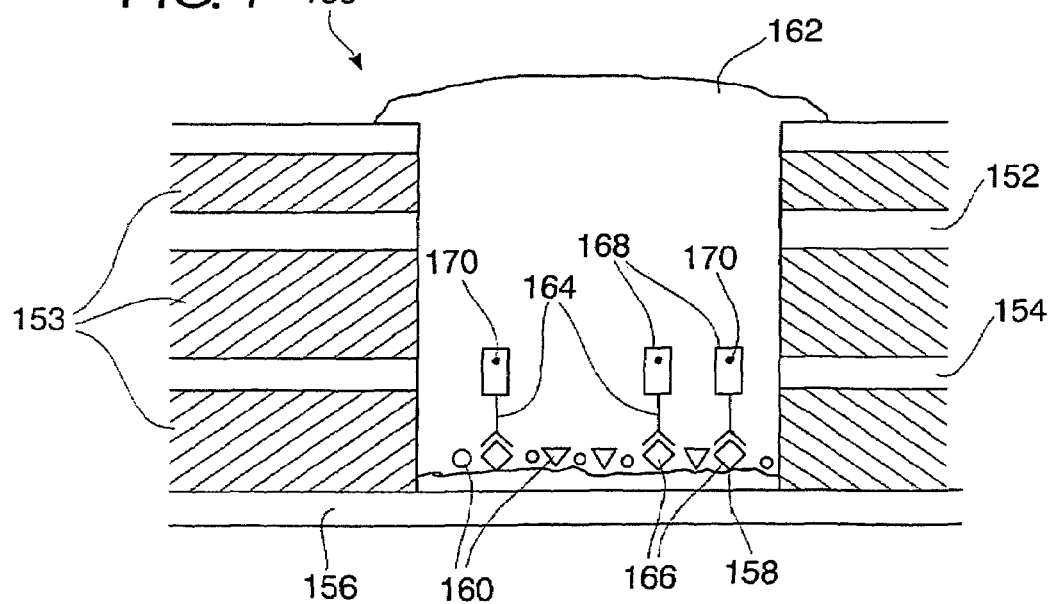

SELF-CONTAINED MICROELECTROCHEMICAL BIOASSAY PLATFORMS AND METHODS

CROSS-REFERENCE TO RELATED APPLICATIONS

This application is a divisional of U.S. patent application Ser. No. 10/253,187, filed Sep. 24, 2002, and claims priority to U.S. patent application Ser. No. 09/978,734, now U.S. Pat. No. 6,887,714, filed Oct. 15, 2001, and claims priority to U.S. Provisional Application Ser. No. 60/240,691, filed Oct. 16, 2000.

BACKGROUND OF THE INVENTION

1. Field of the Invention

The present invention relates to a microvolume electrochemical detection assay. More specifically, the present invention relates to microscale structures having an analyte immobilizing surface and at least one electrode separate from the immobilizing surface. The microscale devices are used in conjunction with an immobilization assay that utilizes an electroactive complex to generate a current that may be detected by the electrode. The small volumes and sensitivity of the assays used in conjunction with microstructures provides an extremely rapid detection method having superior sensitivity to existing methods.

2. Prior Art

There is a great need to miniaturize the analytical methodologies and instrumentation for making rapid and sensitive analyses in biological, environmental, medical and food applications. The interest in decreasing the analysis volume is of value for samples which are precious, expensive, require high spatial chemical resolution, and need improved throughput (e.g. more sample capacity in a smaller space). This does not necessarily demand better detection limits. However, improvements in limits of detection increase sensitivity and accuracy and are also beneficial for dilute analyte in small samples.

One analytical methodology that has been successful at providing the high specificity and selectivity, and which is transferable to small volumes is the immunoassay. This approach has been primarily designed for medical diagnostics, and combines the highly specific antigen (Ag)/antibody (Ab) interaction with the sensitivity of a transducer system that may be optical, radiological, piezoelectric or electrochemical. Immunoassays with electrochemical detection are desirable for a wider range of uses because highly specific and precise current measurements can be performed with simple instrumentation, using opaque device materials, and in colored and turbid samples minimizing prior pre-treatment procedures.

Some of the smallest analyzed volumes have been reported for homogeneous immunoassays, although with poorer detection limits than those of the present invention. One type of small homogeneous assay involves laser induced fluorescence detection combined with fast separation of bound and unbound antibody-antigen complexes in microfluidic systems. Another has the advantages of the simpler electrochemical detection and can be performed in a drop (600 pL). The latter device, however, does not include a separation step, and therefore may be susceptible to interferences from other sample species. Recently, an example of an electrokinetically-driven microfluidic chip for heterogeneous bioassays using about 118 nL volume and assay times below 5 min was reported. Detection was performed with laser induced fluorescence. Complications include modifying the walls of the channel, which affects the electroosmotic flow, and elution of fluorescent-labeled-immobilized species to bring them to the detection site. Low detection limits (pg/mL or fM) were not possible.

Detection immediately adjacent to the surface-immobilized immunocomponents should supply the largest signals with the shortest incubation periods. This has been accomplished with scanning electrochemical microscopy (SECM). Detection limits as low as 5.25 pg/mL have been obtained. However, long total assay times were required (1 h and up). Only the sample volume is small (10's of pL up to several μL) which is spotted onto a surface (and dried, followed by rinsing) or immobilized onto magnetic immunobeads first, which are subsequently transferred to a surface for electrochemical detection. Yet, the enzymatic generation of electrochemically-detected species is carried out on large volumes that must keep both the SECM electrode and the auxiliary/reference electrodes in electrochemical contact. Consequently, this setup is not well-suited for integration with small volume handling or automation and has added complexity due to the SECM instrumentation and operation.

Heterogeneous immunoassays for human serum albumin on a thick-film electrochemical device have been reported. The immunocomponents are also immobilized adjacent to the detecting electrode and small volumes may be used at all stages of the immunoassays. However, unlike the present invention the immunocomponents are attached in a noncovalent fashion to all surfaces (instead of selected ones), the overall dimensions are large (several millimeters) and therefore, the volumes must be larger (30 μL) to cover electrodes and modified surfaces, the area of the immuno active surface exposed to solution is less well defined because it depends upon the size of the drop and wetting properties of the substrate, and the detection (based upon potentiometric stripping analysis) yields detection limits that are higher (0.2 pg/mL).

General immunoassay procedure involves immobilization of the primary antibody (Ab, rat-anti mouse IgG), followed by exposure to a sequence of solutions containing the antigen (Ag, mouse IgG), the secondary antibody conjugated to an enzyme label (AP–Ab, rat anti mouse IgG and alkaline phosphatase) (or a secondary antibody without a label, but followed by a tertiary-antibody with a label and which binds to the secondary one), and enzyme substrate (e.g. p-aminophenyl phosphate; PAPp, where AP converts PAPp to p-aminophenol, PAPR, and the "R" is intended to distinguish the reduced form from the oxidized form, PAPo, the quinoneimine), which is electrochemically reversible at potentials that do not interfere with reduction of oxygen and water (e.g, at pH 9.0, where AP exhibits optimum activity). In addition, the enzyme-generated electroactive species (e.g., $PAP_R$) does not cause electrode fouling, unlike phenol whose precursor, phenylphosphate, is often used as the enzyme substrate. Although $PAP_R$ specifically undergoes air and light oxidation, these are easily prevented on small scales and short time frames. Picomole detection limits for $PAP_R$ and femtogram detection limits for IgG achieved in microelectrochemical immunoassays using $PAP_p$ volumes ranging from 20 μl to 360 μL have been reported previously. In capillary immunoassays with electrochemical detection, the lowest detection limit reported thus far is 3000 molecules of mouse IgG using a volume of 70 μL and a 30 min or assay time. Those skilled in the art will recognize the above described assay as a sandwich-type immunoassay and will appreciate that this is only one of many immunoassays. Alternatives include competitive binding immunoassays and immunoassays utilizing a more general physisabsorbing material other than a primary antibody.

Immunoassays are only one category of a very wide variety of surface immobilization chemical, biological and biochemical detection assays. Northern and southern blot assays are well known techniques for detecting specific polynucleotide sequences. They involve surface immobilization of polynucleotides. Surfaces having one or more lipid layers may be used to immobilize and detect compounds having hydrophobic regions. Molecular interactions may also be taken advantage of to develop surface immobilization chemical detection assays. When two molecules are known to bind to one another, one may be covalently attached to a substrate. The substrate is then exposed to a sample such that the other interacting molecule is given an opportunity to bind to the substrate bound molecule. The substrate is then rinsed leaving only bound analyte on the substrate. A number of detecting methods may then be applied to the surface. Detecting methods include using secondary antibodies as described above, detecting the bi-products of an enzymatic reaction characteristic of the analyte, spectroscopy, fluorescent, electrochemical analysis or other methods known to those skilled in the art.

These assays generally require a laboratory setting. A person wishing to analyze a sample with one of the above described assays most usually sends the sample to a laboratory. Even while in a laboratory, many chemical detection assays take a relatively long period of time.

The disadvantages of immunofluorescence assays (IFA) include their low recovery efficiency, long processing times, the need for highly trained analysts and high cost. In addition, IFA detection often involves the time consuming and skill intensive step of filtering and analyzing water sludge for analytes that have been labeled with a fluorescent antibody. It is also often difficult to distinguish microorganisms from debris bound non-specifically by the antibodies. The procedure is expensive and often takes days to complete.

Flow cytometry is a method used to detect parasitic contamination of water samples. Flow cytometry techniques can quantify microorganisms but involves much preparation, and time and require extremely expensive equipment.

Numerous problems are associated with prior art methods of detecting microorganisms and biological molecules in water and environmental samples. In addition to those mentioned and the general lack of precise, reliable assays, prior art techniques generally require that samples be transferred to a laboratory or to another remote location for the conduct of the assay. Prior art techniques lack the requisite reliability, speed and sensitivity to accurately detect microorganisms and biological compounds in contaminated water samples.

It is crucial that specific, rapid and highly sensitive assays be developed to detect microorganisms and toxins accurately and reliably. The known methods of enzyme immunoassays and immunofluorescence do not fulfill these requirements. The detection, viability or quantity of microorganisms found in water or other environmental samples cannot be reliably determined using prior art methods. There is a need for routine epidemiological surveillance and environmental monitoring that can be conducted on site to provide early detection of the parasite.

It is therefore desirable to provide a method for rapid chemical, biological or biochemical detection of analytes.

It is also desirable to provide a highly sensitive method for detecting low amounts of analyte in a very small amount of sample.

It is also desirable to provide a method for detecting an analyte in a small sample having very high accuracy.

SUMMARY OF THE INVENTION

In the present invention, microstructures are formed by using chemical and/or physical etching processes in combination with thermal evaporation and other layering techniques. Alternating layers of insulating and conducting materials are applied to either a solid or flexible substrate, forming a series of tubular electrodes. The substrate may have preformed holes in order to form pores or may have holes drilled through them after the formation of cavities in order to form pores. The alternating conducting layers serve as electrodes. How deep the wells or pores are depends on how many layers are applied to the initial substrate.

The methods used to form these microstructures allow them to be extremely small. Micropores and microcavities may be formed that are less than a hundred micrometers wide. In fact they may be less than 10 μm wide. The depth of the microstructures ranges anywhere from less than 10 μm to over 100 μm. Microstructures are combined with known chemical detection assays. Surface immobilization assays are especially well suited for these microstructures, although any assays susceptible to electrochemical detection may be combined with these microstructures. Surface immobilization assays are well known to those skilled in the art and include, but are not limited to, immunoassays, northern and southern blots, western blots and incorporation of proteins into lipid layers. Surface immobilization assays are especially advantageous for use in microstructures because the small size of the structures allows for a very short distance between the analyte being captured or recognized and the electrodes being used for electrochemical detection. In addition, the short distance between the electrodes used for detecting the analyte also accelerates both detection and amplification by means of redox cycling. Another benefit of combining surface immobilization assays with electrochemical microstructures is that physisorption of materials used for surface immobilization may be regulated within the microstructure. By applying electrical currents to various electrodes, the location of analyte binding materials within the microstructure may be controlled. This allows a certain material, such as protein binding styrene or primary antibodies, to bind to insulating layers or specific electrodes while preventing physisorption of these molecules to working electrodes.

These microstructures having surface immobilization assays incorporated within them may be further modified by the formation of a lipid bi-layer. Organic compounds may be used to anchor a lipid bi-layer to the rim of a microcavity or, alternatively, to one or both openings of a micropore.

The present invention provides a self-contained, microelectrochemical heterogeneous immunosensor on the smallest volumes reported to date (1 μL for the antigen, 1 μL for the secondary antibody-enzyme conjugate, and 200 nL for the electrochemically detected species) and takes less than 30 min to both complete the assembly of immunoassay components onto the antibody-modified surface and detect enzymatically-generated species. The invention demonstrates the advantage of the close proximity of unmodified electrodes to modified surfaces and their application in the analysis of small volumes. Using a microcavity with individually-addressable electrodes on a microfabricated chip, a primary antibody is selectively and covalently attached at a gold, recessed microdisk (RMD) at the bottom of the microcavity to the free end of self assembled monolayers (SAM's). Non-specific adsorption to the surrounding material, polyimide, of the microcavity device was eliminated. Electrochemical desorption was used to confine the immunoassays activity at the RMD. Alkaline phosphatase, conjugated to a secondary antibody, is used for the enzymatic conversion of the substrate p-aminophenyl phosphate to p-aminophenol ($PAP_R$) and is detectable in less than 30 s using cyclic voltammetry at a ring or tubular nanoband electrode, which is on the wall of the microcavity and immediately adjacent to the modified RMD. A third electrode, also within the region of the microcavity, served as the counter/reference electrode. The invention is suitable for analysis with volumes down to 10 pL.

This self-contained, microelectrochemical enzyme-linked immunosorbent assay (ELISA) device that we report here has the advantages of the SECM systems, but is better suited for small volumes, miniaturization, and for integration with microfluidics (to improve ultra small volume sample handling and speed). Thus, unlike electrochemical immunoassay techniques previously reported, the self-contained electrochemistry in the present invention eliminates the need for an external reference and auxiliary electrode. Because all electrodes are contained in the same small space, ultra small volumes are possible at all stages of the immunoassays. In addition, these devices offer the possibility of further redox cycling (leading to signal amplification) between detecting electrode and other electrodes. The fixed, close proximity between detector and modified surfaces of microbeads or immunobeads makes low detection limits possible and reproducible, and does not require micromanipulators. The response is fast because of the short distance for enzymatically generated species to diffuse from the RMD to the TNB. Finally, separation of the modified surface from the detecting electrode of the invention has advantages over traditional electrochemical sensors where detecting electrodes are also the ones that are modified: (1) the stability of the modified surface is improved because there are no electron transfer events through or changes in potential in that layer, and (2) it allows for a large electrochemical signal because the detecting electrode is bare.

While standard sandwich-type ELISA's such as the one described above are very useful because they are ubiquitous in the art of detection of chemical or biological substances, other immunoassay methods are also suitable for use inside microcavities. Those skilled in the art will recognize that there are a variety of immunoassay methods. Immunoassays may be used not only in sandwich-assays as described above, but also competitive binding assays. Similarly, the primary antibody may be replaced with a variety of chemical compounds. If the analyte is a polynucleotide, it may be desirable to use DNA as the primary probe. The analyte anneals to a segment of the DNA inside the microcavity and the secondary probe will then bind to a segment the polynucleotide analyte. It is also known to utilize compounds that bind to proteins, lipids, carbohydrates, bacteria or viri in place of the primary antibody. Although using general compounds that bind to more general types of molecules will eliminate the specificity provided by the primary probe, the specificity of the overall immunoassay is preserved by use of the secondary probe. Those skilled in the art will recognize that it is common practice to utilize compounds other than the primary probe for binding of the analyte to the assay substrate.

In the present invention, a new immunoassay method has been developed that is especially well suited for use in conjunction with microcavities. The above described methods of utilizing primary antibodies or other compounds for primary probes or capture probes to bind the analyte to substrate may all be used in this newly developed assay. Immunoassays usually are enzyme-linked, thus providing the first 2 letters of the acronym ELISA. The secondary antibody is linked to a catalytic protein, usually by either annealing the protein and antibody genes together or by conjugating them in a chemical reaction. These enzymes conjugated to the secondary antibody react with their substrate to form a product which may then be detected. In the method described above, an enzyme converts PAPP to $PAP_r$. PAP then cycles between electrodes changing back and forth between the oxidized and reduced state. This causes the voltametric signal to be amplified. The present invention includes the development of utilizing metal ion releasing compounds attached to the secondary antibody in place of an enzyme. The released metal ion then may be directly detected by the electrodes within the microcavity. Utilizing a metal releasing compound, such as a metal protein, provides a more reliable and more accurate immunoassay when used in conjunction with a microcavity.

In addition, both alkaline phosphatase and metal binding proteins (electroactive complexes) may both be used in conjunction with polynucleotide hybridization assays, such as northern and southern blots. Electroactive complexes may be covalently attached to DNA or RNA probes used in hybridization assays well known in the art. The probes will bind to analyte DNA within the microcavity. The electroactive complexes may then produce a current that may be measured by the electrodes within the microstructures. This is more accurate and faster than current methods using radioactive isotopes or fluorescing compounds. In addition, it is much safer than the commonly used radioactive isotopes.

The present invention also provides for the detection of microorganism within an aqueous solution. The primary antibodies specific for a particular microbe may be used to immobilize a single microbe within a microcavity. This allows for rapid electrochemical detection utilizing a secondary antibody having a covalently bound electroactive complex. This rapid detection of microbes is a significant advantage over current existing methodologies that often take 24 hours or longer to detect microorganisms.

Another significant improvement of the present invention is its ability to determine whether or not detected microorganisms are alive or dead. Once microorganisms are detected using immnuoabsorbent techniques within a microstructure, they may be heat shocked. Heat shocking causes microorganisms to release polynucleotides. Hybridization assays either within the same microstructure or in one to which the analyte solution is transferred may then be used to detect the released polynucleotides. Dead microorganisms do not release polynucleotides specific for the production of heat shock proteins when heated. Assays that are capable of determining not only the presence, but also viability of microorganisms are especially useful in water treatment facilities.

Because the microstructures are so small, multiple, individually addressable microstructures may be formed in a single chip. When only one microstructure is used for an assay, such multi structure arrays may be re-used as many times as there are microstructures. Arrays are also useful when detecting very low concentrations of analytes. The multiple microstructures may be used simultaneously. This method of sampling provides for a highly accurate assay of analytes present in very low concentrations.

This invention makes smaller volumes no more difficult to analyze than macrovolumes because all of the electrodes are prefabricated within the same small volume, thereby allowing self-contained electrochemistry to occur. Not only can heterogeneous immunoassays in such electrochemical systems be applied to smaller sample volumes than previously possible, but they also offer better detection limits, sensitivity, and speed because of the close proximity of electrodes and modified surfaces. In addition, a new polyimide passivation protocol protects the detecting electrodes until they are needed and prevents immuno active physisorption to undesirable locations. These procedures allow fabrication of accurate and reliable immunosensor arrays. This procedure is also promising for modification in enclosed microfluidic devices where photo patterning may not be convenient.

BRIEF DESCRIPTION OF THE DRAWINGS

FIG. 5 shows a schematic diagram of a microcavity being used in conjunction with a sandwich type immunoassay;

FIG. 6 shows a schematic diagram of a microcavity being used in conjunction with a competitive binding immunoassay;

FIG. 7 shows a schematic diagram of a microcavity being used in conjunction with an immunoassay utilizing a protein adhesion layer instead of a primary antibody;

DETAILED DESCRIPTION OF THE INVENTION

Figure 1:
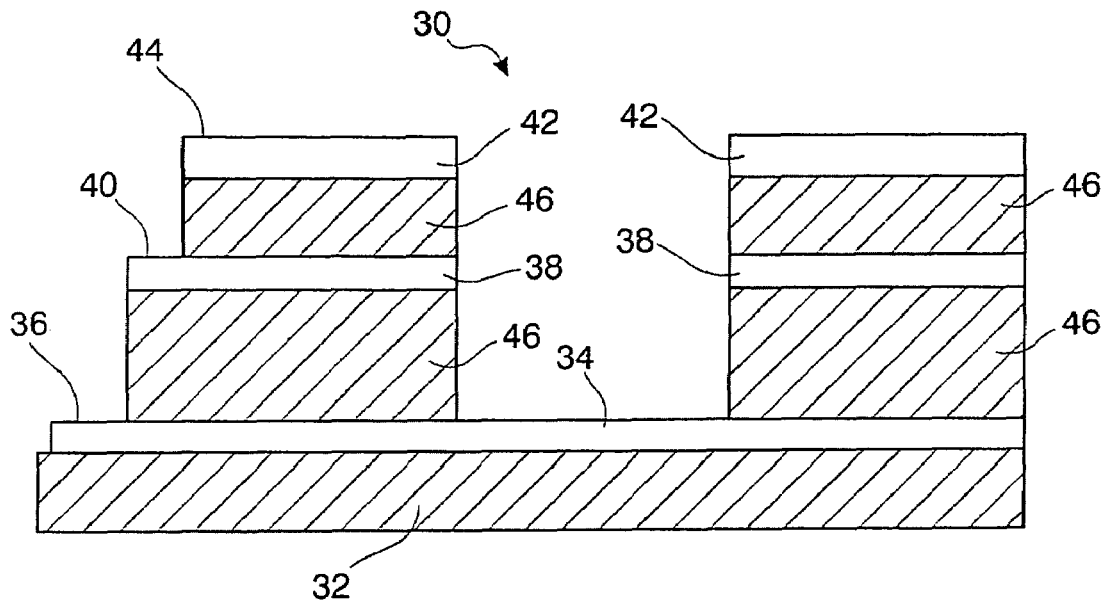
FIG. 1 shows a cross sectional diagram of a microcavity.

"Microstructures" refers to microcavities and micropores having alternating insulating and conducting layers where at least one of the conducting layers serves as a working electrode to detect current produced by electroactive complexes. They generally have circular cross sections, but may also be polygonal. They may be formed on rigid or flexible substrates.

"Microassay" means any of a variety of immobilization assays performed within a microstructure and detected by electrochemical methods described herein. These assays include, but are not limited to, sandwich type and competitive binding immunoassays, including those utilizing microimmunobeads, polynucleotide hybridization assays, such as northern and southern blots, and protein binding assays.

"Analyte" means any chemical compound, biomolecule, bacteria, virus or portions thereof susceptible to immobilization assays including immunoassays and polynucleotide hybridization assays.

"Electroactive complex" refers to any protein or other molecule capable of producing an electric current when activated by any of a number of controllable parameters. This includes both redox enzymes, capable of either oxidizing or reducing a substrate molecule, and metalloproteins, capable of releasing metal ions. Synthetic molecules, such as dendrimers that bind several metal ions, are also included.

"Sample" means a composition that may or may not include an analyte. A sample may be either aqueous, dissolved in an organic solvent or a solid sample that may be dissolved in either water or an organic solvent. Prior to being applied to microassay structures, a solid sample will need to be dissolved in a suitable solution capable of dissolving a suitable electrochemical species.

"Microassay structure" means a microstructure that has been adapted to perform a microassay.

"Primary analyte binding material" refers to any of a variety of compounds and biomolecules used in immobilization assays to bind one or more analyte to a surface. These include but are not limited to primary antibodies, lipid layers, protein binding materials such as styrene, polynucleotides and combinations thereof.

"Secondary Analyte Binding Material" is any material capable of binding to an analyte and being covalently bound to an electroactive complex. This includes secondary antibodies as used in ELISA's and polynucleotide probes as used in hybridization assays.

"Activating agent" means any change in a controllable parameter that induces an electroactive complex to generate a current electrochemically. This includes the addition of a redox substrate, change in pH, change in temperature, application of an electric charge, change in concentration of a particular molecule and other factors known to those skilled in the art.

The present invention includes a novel surface immobilization electrochemical assay. The invention combines known surface immobilization and molecular interaction techniques with a novel electrochemical detection method in a microstructure. Any of a number of analyte binding materials are applied to the substrate of an assay structure. A sample to be tested for a specific analyte is then introduced to the assay structure. Any analyte present is then placed under the proper conditions in which it may bind to the analyte binding material. The assay structure is then rinsed to remove all materials other than bound analyte and assay solution. A secondary analyte binding material is then added to the assay structure under conditions allowing it to bind to the bound analyte. The assay structure is then rinsed again such that only the bound analyte and secondary analyte binding material remain on the assay structure. The assay structure is then immersed in either the same or a second assay solution. The secondary analyte binding material has a covalently bound electrochemically active molecule. When activated, the electrochemically active molecule creates a current within the assay structure. After the secondary analyte binding material is given sufficient time to bind to any analyte present, the assay structure is again rinsed to remove any secondary analyte binding material that is not bound analyte. The electrochemically active complex is then activated. If analyte is present, then a current will be created within the assay structure. The strength of the current is directly related to the amount of analyte present.

Those skilled in the art will recognize that there are at least two current detection methods that utilize a primary and secondary analyte binding material. Perhaps the most common is the "ELISA", utilizing a primary antibody and a secondary antibody. The difference between the present invention and the existing ELISA schemes is the present invention's rapid detection of an electrochemically active molecule within a self-contained microstructure having an array of wells or pores with microelectrodes incorporated therein. Existing ELISA's utilize a fluorescent tag, an isotope label or enzymes that act upon a substrate to cause a color change. These existing methods are substantially less accurate and more time intensive than the present invention.

Another known detection method is the hybridization assay. A DNA probe is attached to an assay structure that has a complementary segment to the analyte or target DNA. A secondary probe labeled with an enzyme or any other reporter molecule is then added to the assay that also has a complementary segment to a different section in the target DNA binds. These hybridization assays when performed in the conventional way are subject to the same shortcomings as current ELISA assays. They are less accurate and more time intensive than the present invention.

Those skilled in the art will recognize that a variety of electrochemically active molecules will be suitable for the present invention. The present invention contemplates the use of redox enzymes as well as metalloproteins. A redox enzyme, such as alkaline phosphatase reduces a substrate. The reduced substrate is then oxidized by a working electrode, thereby creating a current. The substrate is again reduced by the electrochemically active enzyme and cycles back the electrode. This redox cycling amplifies the current and allows for detection of extremely low concentrations of analyte. Those skilled in the art will appreciate that alkaline phosphatase is only one of many suitable redox enzymes. Any enzyme capable of reducing a substrate rapidly will be a suitable enzyme. In addition to redox enzymes, metaloproteins are also especially well suited for the present invention.

Those skilled in the art will recognize that there are a wide variety of both proteins and organic compounds capable of binding to metal ions. There are a number of well studied metalloproteins capable of binding to various metals such as iron, zinc, magnesium and copper to name a few. The genes that encode for these proteins may be attached to a secondary antibody in the same way that enzymes are attached to secondary activating antibodies. After the secondary antibody binds to the analyte and the microcavity is rinsed, the metalloprotein is treated so that it releases the metal ion incorporated within it. The metal ion attached to the metalloprotein may be released in a variety of ways, depending on the protein used. Many metalloproteins release the incorporated metal ion upon a change in pH. This may be accomplished either by adding buffer to the solution or utilizing the electrodes within the microcavity themselves to release protons in the solution electrolitically. Other metalloproteins release their metal ions upon reaction with a secondary compound that may be added to the immunoassay subsequent to the rinsing step. Yet, other metalloproteins release their metal ions in the presence of chelating agents, such as ethylenediaminetetraacetic acid (EDTA). Those skilled in the art will recognize that these methods of coaxing metalloproteins to release their incorporated metal ions are well known to those skilled in the art.

It may also be desirable to synthesize novel electroactive complexes to attach to the secondary probe. Those skilled in the art of protein engineering will recognize that there a number of common amino acid sequences capable of binding to metal ions. A Few examples are zinc fingers, cysteine loops, heme groups and the His $X_3$ His and His Pro Phe His sequences. These amino acid sequences may be added to existing, known polypeptides or may be incorporated into novel peptide sequences and spliced onto secondary antibodies. So long as the electroactive complex is capable of forming a stable bond with a metal ion or electroactive molecule and may be induced to release the metal ion/electroactive molecule by the addition of a compound, change in pH, change in temperatures or other means easily adaptable for use with microcavity or micropore assays.

One of the advantages of using a metal binding electroactive complexes is that it provides a metal ion that easily cycles between electrodes as it undergoes reduction and oxidation or vice versa. This creates an automatic redox cycling reaction. Because of this, amplification is inherent to the assay. This eliminates the need for additional chemical amplification steps. Those skilled in the art will realize that this greatly simplifies chemical detection.

There are a variety of metalloproteins known to the field of biochemistry. These include metallthionin, ferritin, heme, dendrimer, and staph nuclease. Those skilled in the art will recognize that these are only a very few of the many polypeptides capable of binding to metal ions. When using one of these polypeptides as an electroactive complex it may be desirable to splice or covalently bind several copies of the carrier species gene to the end of the secondary antibody gene. This would form a polypeptide polymer tail on the secondary antibody and increase the number of metal ions for use in the microimmunoassay sensor. Metalloproteins are especially well suited for redox cycling amplification by means of a counter electrode.

Those skilled in the art will appreciate that there are a variety of activating agents. Which one is used will depend on the electroactive complex used. It is known that some metalloproteins release metal ions when the pH of the solution is altered. Other metalloproteins release metal ions when other parameters are changed. These parameters include, but are not limited to, change in temperature, addition of a substrate or ligands, application of an electrical current and application of electromagnetic radiation. Which metalloprotein and which activating agents are utilized will depend on a variety of factors including, but not limited to, the analyte being studied, the material utilized to immobilize the analyte, reaction temperature, reaction pH and the concentrations of various reagents and other ingredients in the solution.

One of the significant advantages of the device disclosed herein is the fact that it makes use of microcavities and micropores. The small size of these microstructures, less than a hundred micrometers in diameter, results in the electrodes being very close to one another. The short distance between electrodes greatly increases both the speed at which sensing occurs and the sensitivity of the device due to the restriction of diffusion of the species to the bulk solution and to the small electrodes confined within the picoliter volume of the microcavity. Alternate layers of insulator and conductor are applied to a substrate to create the microcavities. The substrate may be either rigid as when a silica chip is used or flexible, as when a polyimide film is used. Chemical and physical etching processes and photolithography may be used to etch a pattern into the alternating layers of conductor and insulator onto a substrate. Those skilled in the art will recognize chemical etching as a common process. The process of forming microstructures on rigid silica wafers is described in the detail below.

FIG. 1 shows a cross sectional diagram of a basic microcavity. Substrate 32 may be any of a variety of materials such as glass, ceramic, silica or polyimide film. Flexible substrates may be used to form microstructures on flexible surfaces while rigid substrates are used to form microstructures on rigid surfaces. Conducting layer 34 is then applied to substrate 32 using thermal evaporation, sputtering or other methods known to those skilled in the art. Conducting layer 34 may be gold, copper or other suitable conducting materials. Depending on the materials used, it may be desirable to apply a chromium or any other adhesion layer prior to applying conducting layer 34. Standard photolythographic techniques are utilized to apply alternating insulating layers 46 with conducting layer 38 sandwiched between them. Final conducting layer 42 is applied to give structural support to the microstructure. Top layer 42 may also double as a counter or reference electrode. Contact pads 36, 40 and 44 are used to apply current to conducting layers 34, 38 and 42 respectively.

Figure 2:
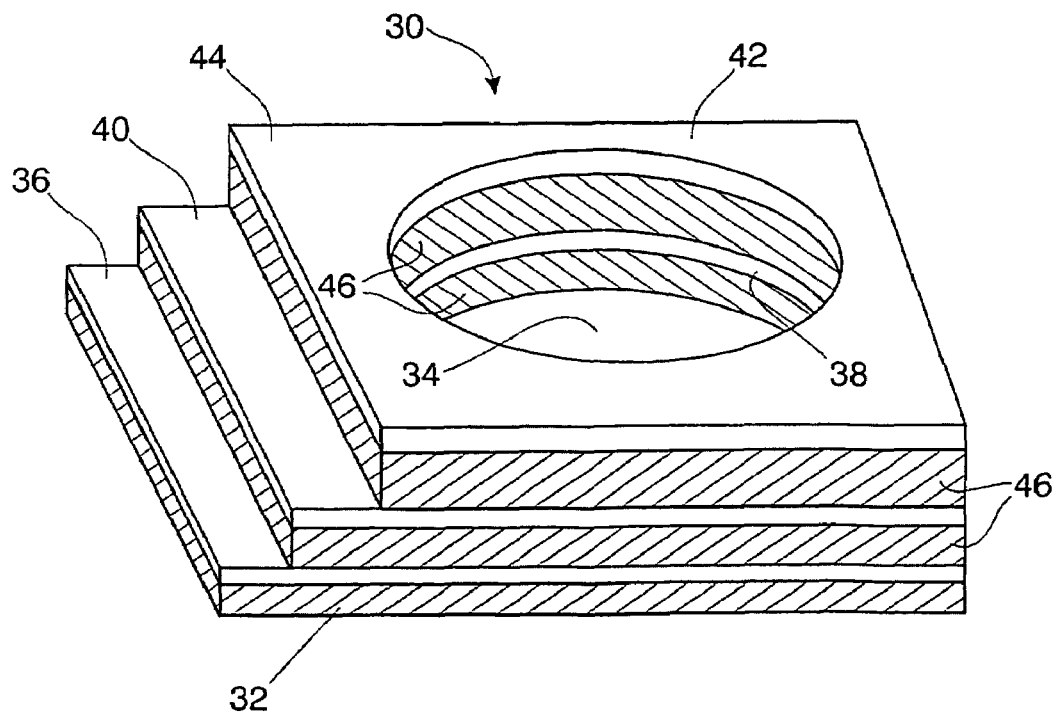
FIG. 2 shows a perspective diagram of a microcavity.

FIG. 2 shows a perspective diagram of the microstructure shown in FIG. 1. In FIG. 2 it can be seen how conducting layer 38 forms a tubular nanoband electrode within the microcavity. Current photolythographic and etching techniques allow microcavity 30 to be less than 10 mM in diameter. FIGS. 1 and 2 show a circular microcavity. However, those skilled in the art will appreciate that a microcavity cross-section may have a variety of geometries, including any polygon desired. While this embodiment shows three conducting and 2 insulating layers, those skilled in the art will also appreciate that additional layers may be added to the microstructure so that as many insulating and conducting layers as is desired may be applied.

When desiring to form micropores on a flexible polyimide film, it is often desirable to form a pore in a film prior to the layering and etching process. Pores in a polyimide film are formed by an excimer laser. As the laser passes through the film, it slowly disperses and the resulting pore has a funnel shape. The average diameter of the pore where the laser enters the film is 70 mm, and the average diameter where the laser exits the film is 30 mm.

Figure 3:
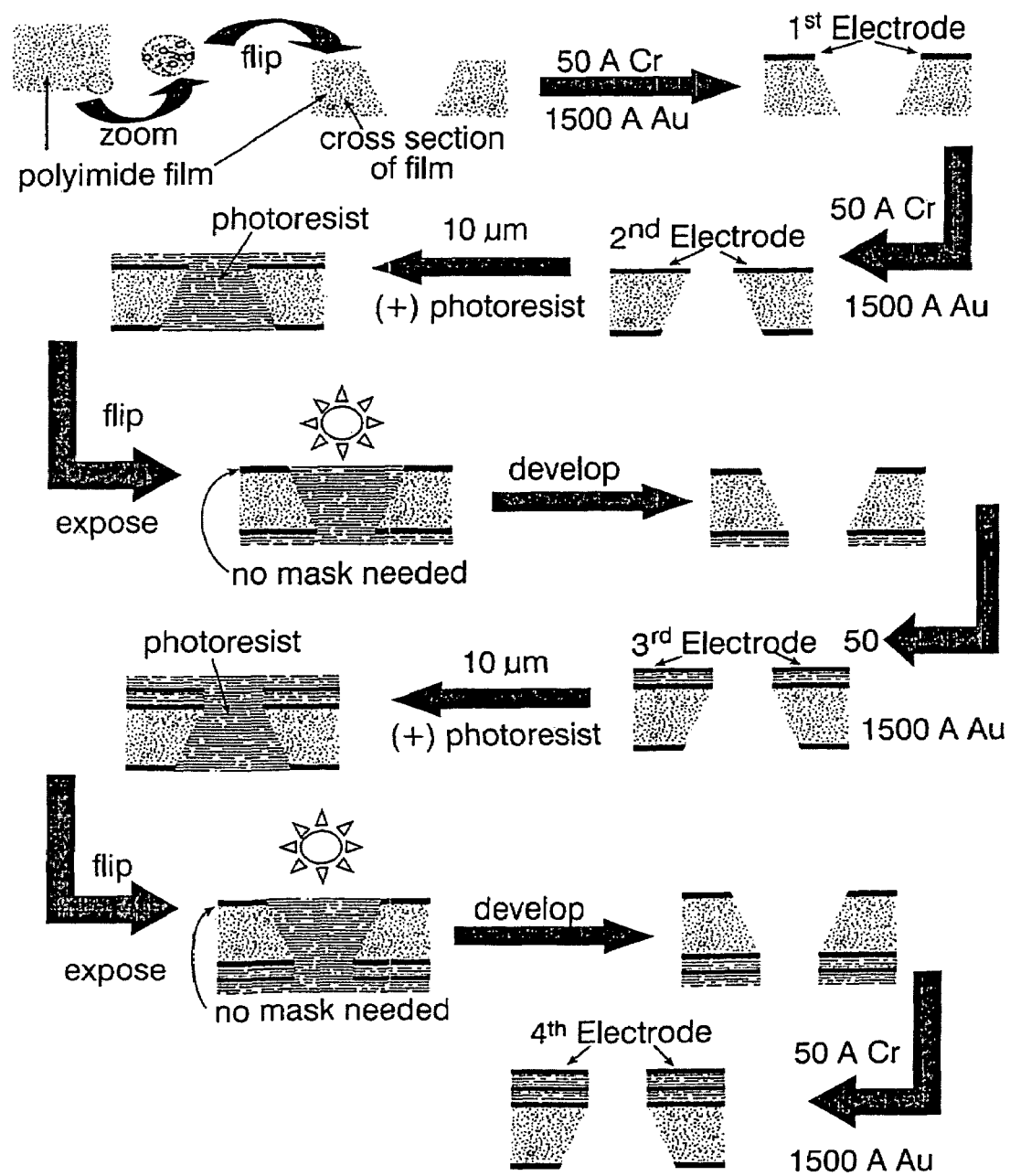
FIG. 3 shows a flow chart of the fabrication procedure utilized to form electrodes in a micropore on a polyimide film.

A flow chart for the fabrication procedure is shown in FIG. 3. The polyimide film was cut to a workable size, put into a carrier to pattern the gold layer, and placed at a vertical angle in the thermal evaporator to reduce the chances of shorting between gold layers. A 50μ chromium film is applied to the polyimide film by thermal evaporation in order to form an adhesion layer. Next, a 1,500 angstrom gold film was deposited also by thermal evaporation. The process is then repeated on the opposite side of the film.

When forming a microstructure around a pore in a polyimide film, the photoresist from the etching process is itself used as the insulating layer. A 10 micrometer thick positive photo resist film is applied to the polyimide film. When the positive photoresist is exposed to UV light, it washes away in developer solution. If the photoresist is covered to block the UV light, it will not develop away in the solution. After application of the photoresist to both sides of the film, one side is exposed to UV light. This way, only the photoresist on the side facing the UV light and the photoresist within the pore itself develop away in solution. This leaves an insulating layer on the side of the film facing away from the UV light source. Thermal evaporation is used to apply a subsequent conducting layer to the side having photoresist insulator. This process is repeated to form as many alternating conducting and insulating layers as is desired.

Whether a cavity or pore is more desirable will depend on the environment in which the microstructure is to be used. Similarly, whether a rigid or flexible microstructure is formed will also depend on the purpose to which the microstructure is to be used. Pores may prove more desirable in devices that use flow through analysis. They may prove especially suitable for microfluidic devices. Flexible micropores and microcavities may prove more suitable in medical or biological testing applications.

Figure 4:
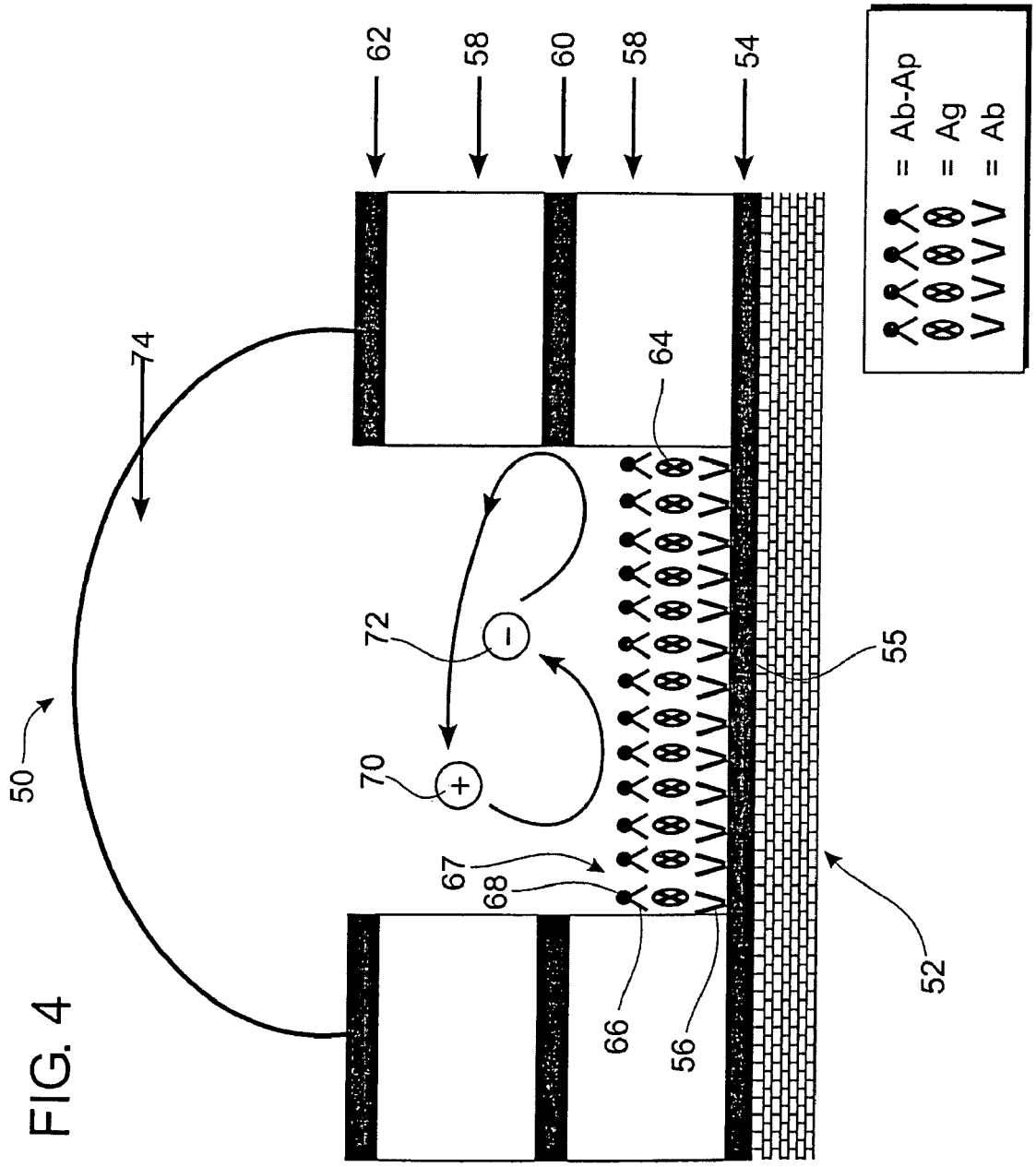
FIG. 4 shows a diagram of a microcavity used in conjunction with a sandwich type ELISA, where the secondary antibody is bound to alkaline phosphatase.

FIG. 4 shows a diagram of a microcavity adapted for use with a sandwich type ELISA microassay. Microcavity 50 is formed by first applying conductive layer 54. Insulating layers 58 have been formed with conducting layers 60 sandwiched between them to form a tubular nanoband electrode. Finally, conducting layer 62 is applied to add structure and to provide a reference/counterelectrode. Droplet 74 is a solution in which the immunoassay is performed. Any solvent is suitable for droplet 74 so long as it does not denature the proteins and antibodies within it. Primary antibodies 56 may be attached to recessed micro disk 55 formed at the bottom of microcavity 50 by insulating layer 54. This may be done by first attaching a self assembling monolayer not shown to conducting layer 54 and then covalently binding primary antibodies 56 to the self assembled monolayer.

After primary antibodies 56 have been attached to recessed microdisk 55, a sample solution containing analyte 64 is applied to microcavity 50. After sufficient time under proper conditions has been allowed for analyte 64 to bind to primary antibody 56, the microcavity 50 is rinsed to remove all of the sample solution except for bound analyte 64. Secondary antibodies 67 are then added to microcavity 50. Secondary antibody 67 is comprised of two parts, and analyte 64 specific antibody portion 66 and a covalently bound electroactive complex 68. In this embodiment, electroactive complex 68 is a redox enzyme.

Once secondary antibodies 67 have been given time to bind to analyte 64, microcavity 50 is again rinsed to remove excess secondary antibody 67. An activating agent is then introduced to the microcavity. In this embodiment, the activating agent is an oxidized form of a redox compound 70. Redox enzyme 68 reduces the redox compound into its reduced form 72. The reduced redox compound 72 discharges an electron to conducting layer 60 and returns to its oxidized state 70. Redox enzyme 68 then reduces the compound again, causing the redox compound to cycle between reduced and oxidized states, thus amplifying the signal. The current introduced to electrode 60 may then be measured which in turn allows measurement of the amounted analyte from which the concentration of analyte in the original sample solution may be calculated. Those skilled in the art will appreciate that redox cycling may also be facilitated or enhanced by applying a positive charge to a second electrode such as counter/reference electrode 62.

The close proximity of electrodes 60 to the surface on which the assay is performed greatly increases the rate of detection. The extremely small volume of microcavity 50 also contributes to a very fast reaction rate.

FIG. 5 shows an alternative embodiment of a microstructure adapted for a sandwich type ELISA microassay. In this embodiment, the cavity was layered onto solid substrate 122. A glass slide 106 covers microcavity 100 so as to prevent evaporation. With extremely small volumes such as these, evaporation can become a problem. Primary antibody 108 is covalently bound to the self assembled monolayer 123. Analyte 110 is bound to primary antibody 108. Analyte 110 is also bound to secondary antibody 112 which is covalently linked to metalloprotein 114. In this embodiment, metalloprotein 114 is bound to four manganese ions. After the second rinse to remove excess secondary antibody, metalloprotein 114 is activated so as to release its four manganese ions. These ions then begin to shuttle electrons from counter electrode 102 to working electrode 104. This electron shuttling between electrodes results in redox cycling that amplifies the signal. By measuring the current, the concentration of analyte may be calculated. The embodiment in FIG. 5 illustrates the improvement this invention makes over standard enzyme linked immunoassays. By linking a secondary antibody to a metalloprotein, especially one binding to several metal ions, the secondary antibody becomes uniquely adapted for electrochemical detection within a microstructure. The redox cycling induced in the embodiments shown in FIGS. 4 and 5 further improve the immunoassays by increasing both sensitivity and accuracy of analyte detection.

While standard sandwich-type immunoassays are very useful because they are ubiquitous in the art of chemical detection, other immunoassays methods may be more suitable for use inside microcavities. Those skilled in the art will recognize that there are a variety of immunoassays methods. Immunoassays may be used not only in sandwich-assays as described above, but also competitive binding assays as shown in FIG. 6.

Here, microcavity 100 again has primary antibodies 108 covalently linked to self assembled monolayer 123. After the sample has been applied to microcavity 100, the microcavity is then rinsed. Next, competitive binder 120, covalently linked to electroactive complex 114, is added to microcavity 100. Competitive binder 120 binds to primary antibodies 108 that do not have analyte 110 bound to them. The electroactive complex 114 is then activated so as to release bound metal ions 116, which begin redox cycling between electrodes. With this type of assay, the weaker the current, the stronger the initial analyte concentration.

The primary antibody may be replaced with a variety of chemical compounds. If the analyte is a polynucleotide, it may be desirable to use DNA in place of the antibody. The analyte will then anneal to the DNA inside the microcavity and the secondary antibody will then bind to the polynucleotide analyte. It is also known to utilize compounds that bind to proteins, lipids, carbohydrates, bacteria or viri in place of the primary antibody. Although using general compounds that bind to more general types of molecules will eliminate the specificity provided by the primary antibody, the specificity of the overall immunoassays is preserved by use of the secondary antibody. Those skilled in the art will recognize that it is common practice to utilize compounds other than the primary antibody for binding of the analyte to the assay substrate.

FIG. 7 shows another type of immunoassays well suited for use in microcavities. The microcavity is built upon substrate 156 which may be either a solid silica substrate or a flexible polyimide substrate. Electrodes 152 and 154 are separated by insulating layers 153. In the bottom of microcavity 150 is a protein adhesive layer 158. Those skilled in the art will recognize that there are a variety of materials to which all polypeptides adhere. In this immunoassays, the sample is applied to the microcavity and analyte 166 binds to layer 158, as do other proteins 160. Secondary antibodies 164 are bound to carrier species 168 that each contain a metal ion 170. Secondary antibodies 164 bind to analyte 166. Electroactive complexes 168 are then activated to release ions 170 that create a current between electrodes 152 and 154. This type of assay is similar to that found in FIG. 5, except that the substance attached to the substrate binds several proteins and is not specific to one molecule as primary antibody 108 is.

Figure 8:
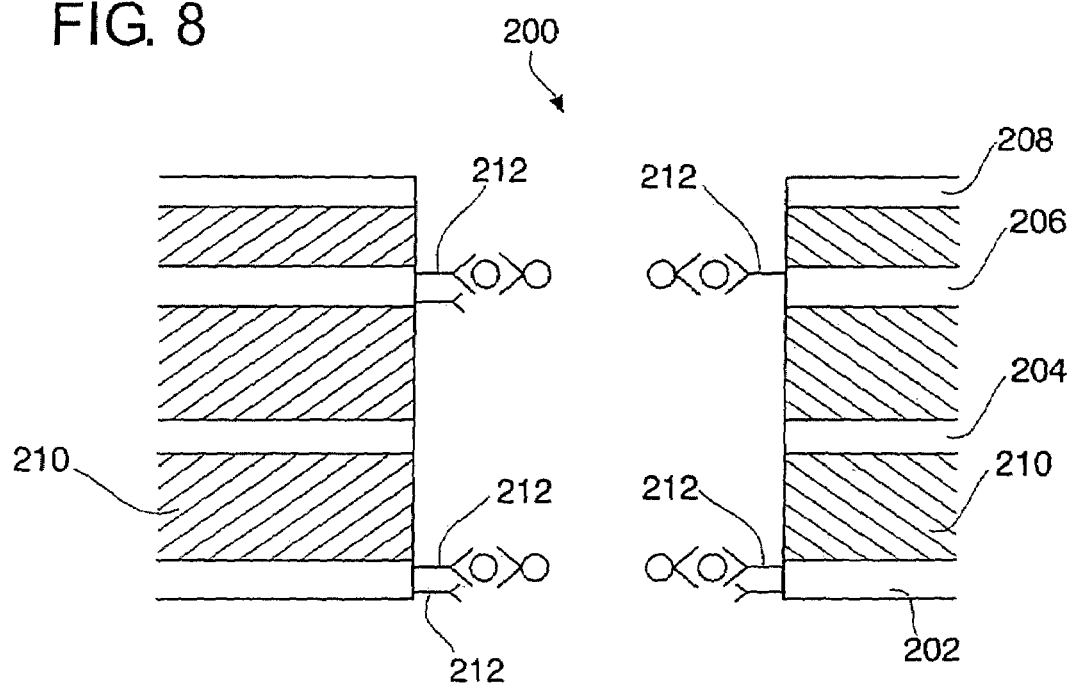
FIG. 8 shows a schematic diagram of a micropore being used in conjunction with a sandwich type immunoassay.

FIG. 8 shows immunoassays micropore 200. Substrate 202 may be either a rigid silica wafer or a flexible polyimide film. Alternating layers of insulator 210 and electrodes 204 and 206 are applied according to the methods described herein. Final layer 208 is comprised of conductor material and provides stability to the microstructure. Primary antibodies 212 are attached to the interior of the micropore. The solution to be tested may be run either over or through pore 200. The immunoassays utilizes the same as that found in FIG. 5, a sandwich immunoassays. Analyte binds to primary antibodies 212, secondary antibodies bind to analyte, and the electroactive complexes attached to the secondary antibody is activated to release its ions and induce an electrical current. Those skilled in the art will realize that any of the immunoassays described herein are as suitable for use in micropores as they are for use in microcavities.

As these microstructures are very small, evaporation becomes a serious consideration. It may therefore be desirable to cover the microcavity, thus preventing evaporation. It may also be desirable to suspend a film or lipid bilayer across the top of a microcavity or micropore. Transport proteins may be inserted into lipid bi-layers and the analyte studied may be a transported compound. In this situation, the microsensing device described herein may be used to detect and measure the activity of various membrane transport proteins.

Figure 9:
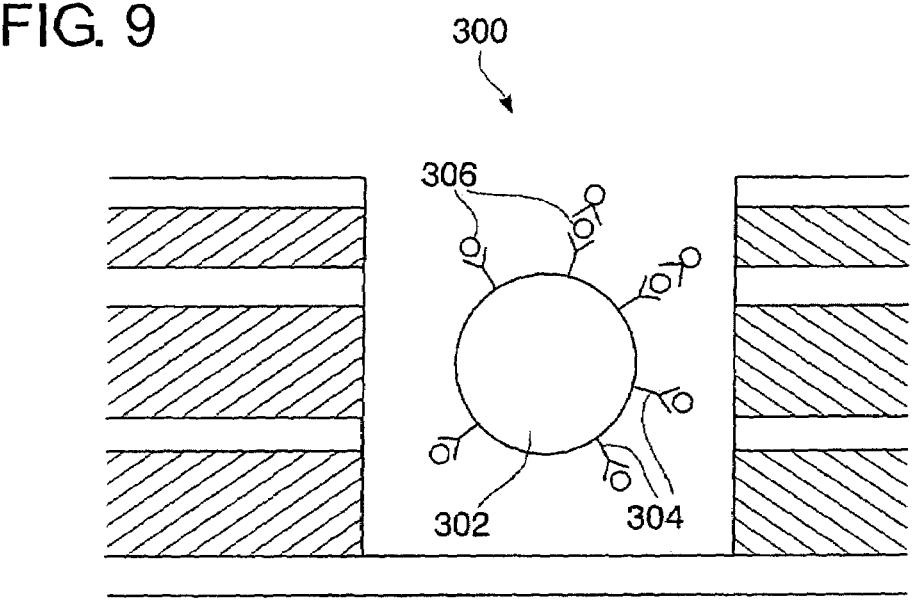
FIG. 9 shows a schematic diagram of a microimmunobead being used in conjunction with a microcavity.

FIG. 9 illustrates use of a microcavity in conjunction with an immunobead. Use of immunobeads allows the reaction of binding the analyte to the primary antibody to take place somewhere besides the microstructure. After the analyte has bound to the primary antibodies on the immunobead, the immunobead is then inserted into the microcavity and the immunoassays is carried out to completion as described above. Those skilled in the art will appreciate that immunobeads may be used either with sandwich or competitive binding immunoassays. Those skilled in the art will also realize that microbeads may be used in other types of assays.

In FIG. 9, immunobead 302 is covered in primary antibodies 304 which bind to analyte 306. Immunobead 302 is then inserted into microcavity 300. Microcavity 300 may be lined with material that facilitates physiabsorbtion of microbeads. Also, magnetic fields may be applied in order to coax microbeads into microcavities.

Figure 10:
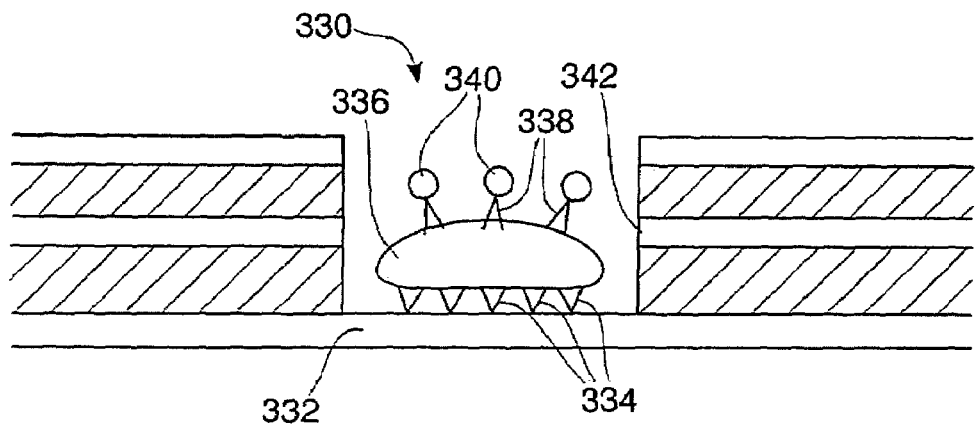
FIG. 10 shows a diagram of a microstructure used in conjunction with a sandwich type immuno assay used to immobilize and detect a microorganism.
Figure 12A:
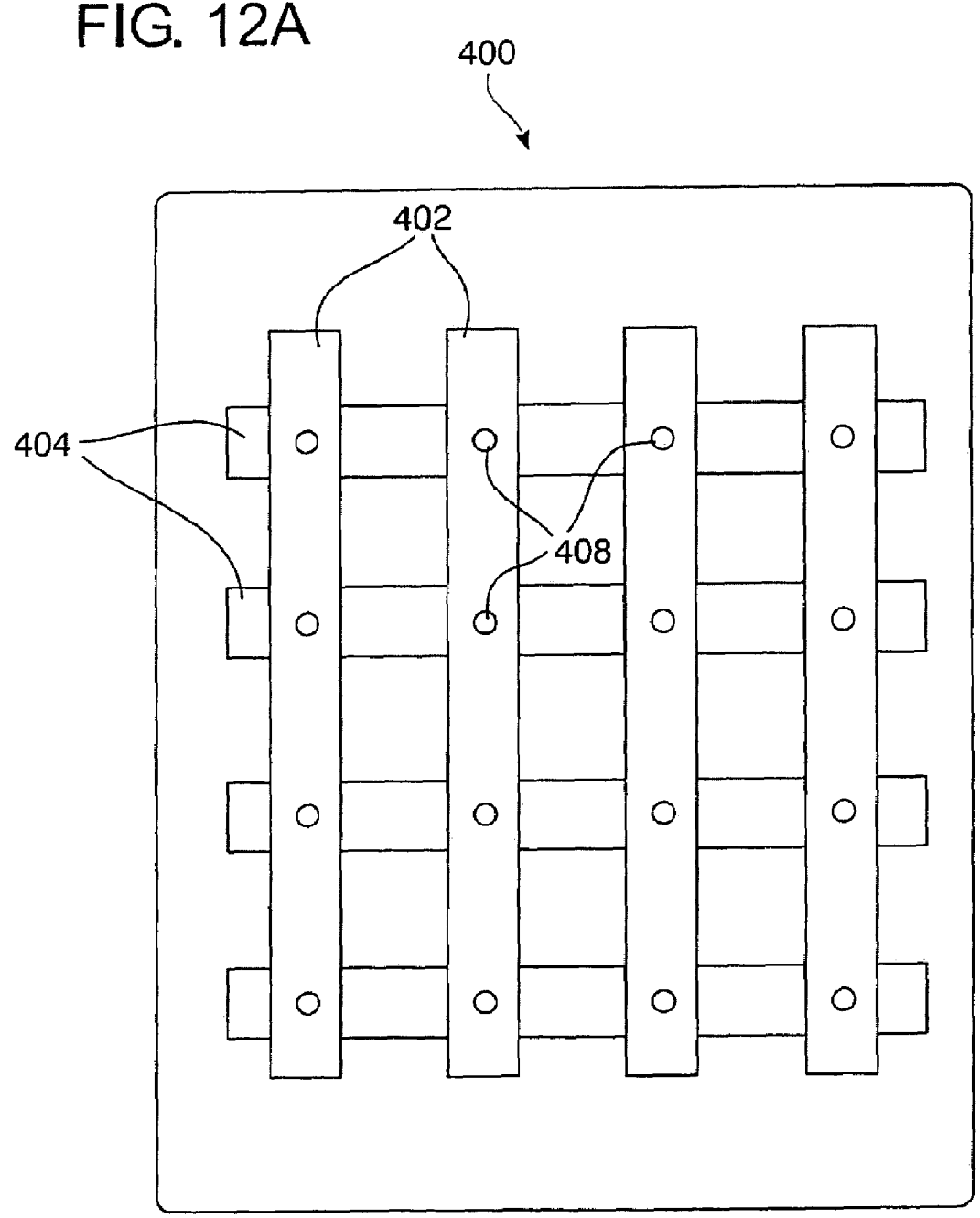
FIG. 12A shows a schematic diagram of an array of microcavities.

FIG. 10 illustrates the use of a microassay to detect a microorganism. In this embodiment, microbe 336 is immobilized within microcavity 330 by binding to primary antibodies 334 which are attached to substrate 332. After microbe 336 has been immobilized within microcavity 330, secondary antibodies 338 having covalently attached electroactive complexes 340 are then applied. Secondary antibodies 338 bind to microbe 336 and electroactive complexes 340 are then activated. This results in a current being discharged into electrode 342 which may then be measured in order to calculate the concentration of microbes 336. Because only 1 or 2 microbes would fit inside the smaller microcavities, arrays such as those shown in FIG. 12 are especially useful for this type of microbe detection. Many water born pathogens, such as *C. Parvum, E. Coli*, cholera, anthrax and other pathogens known to those skilled in the art, may be quickly, easily and inexpensively detected using the present invention.

It is possible to use electroactive complexes in conjunction with assays besides immunoassays. For example, probes for Northern and Southern blot oligonucleotides may be bound to these electroactive complexes. The blot assay may then be performed within a microcavity. This not only provides for very sensitive detection, it is much safer than standard Northern and Southern blots that utilize radioactive isotopes. Those skilled in the art will see a great advantage to a faster, safer type of polynucleotide assay.

Figure 11A:
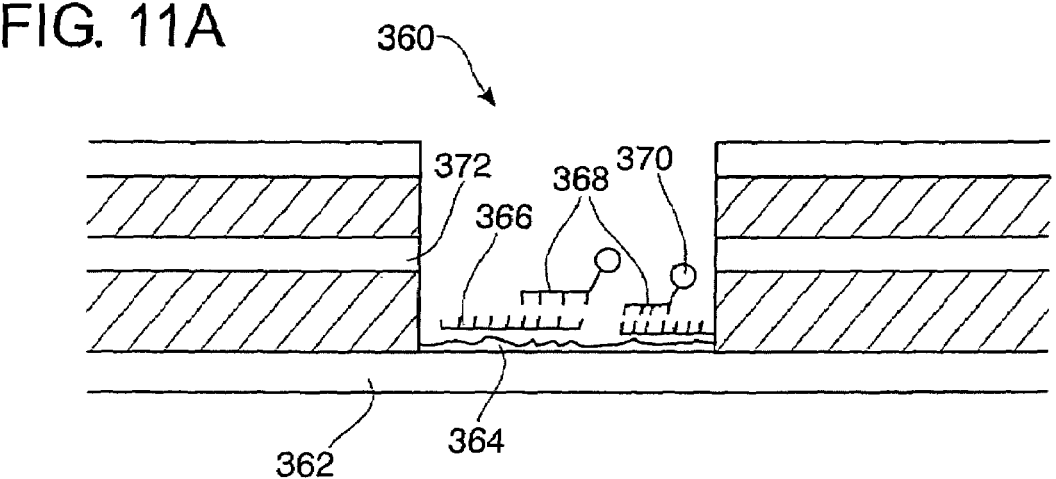
FIG. 11A shows a microcavity used in conjunction with a DNA hybridization assay, wherein the probe has an electro active complex covalently attached to it.

FIG. 11A illustrates a hybridization microassay performed within a microstructure. Microcavity 360 has polynucleotide binding material 364 attached to substrate 362. Polynucleotides 366 from a sample are applied to microcavity 360 after being denatured. They then bind to DNA binding material 364. Those skilled in the art will appreciate that it is sometimes desirable to denature nucleotides 366 after binding to nucleotide binding material 364. Next, probes 368 having covalently attached electroactive complexes 370 are applied to microcavity 360. Probes 368 anneal to portions of polynucleotides 366 that are complimentary to the sequences of probes 368. Microcavity 360 is then rinsed of excess probe 368 and electroactive complexes 370 are then activated in order to generate a current in working electrode 372. This current may be measured in order to calculate the concentration of polynucleotides that are complimentary to probes 368. Many microbes release specific mRNAs into surrounding solution. Therefore, these types of hybridization assays may also be used to detect of presence of microbes in aqueous or other solutions.

Figure 11B:
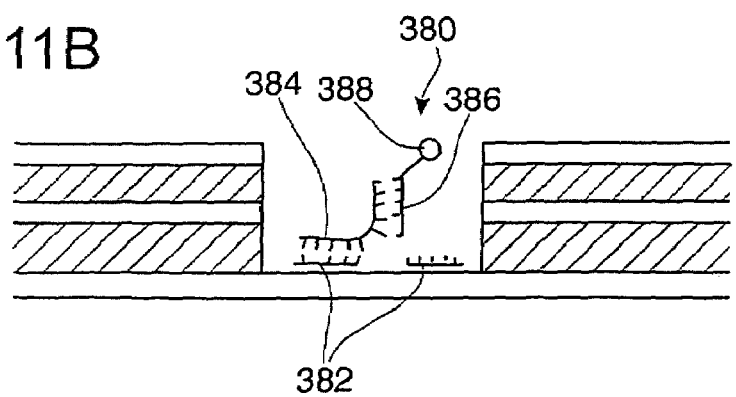
FIG. 11B shows a microcavity used in conjunction with an alternative DNA hybridization assay, wherein the secondary probe has an electroactive complex covalently attached to it.

FIG. 11B illustrates an alternative hybridization assay for use in a microstructure. Microcavity 380 has primary probes 382 bound inside it. When analyte solution possibly having analyte bacteria in it is heat shocked and the solution is placed in microcavity 380. Heat shock polynucleotides will then partially bind to primary probes 382. Primary probes 382 are complimentary only to a portion of the heat shock polynucleotides. This allows a secondary probe 386 to bind to another portion of the heat shocked polynucleotide. The secondary polynucleotide has an electroactive complex 388. Once the secondary polynucleotide has been given time to bind the heat shocked polynucleotide, the electroactive complex is activated so as to generate a current. If there are no heat shock polynucleotides present, the secondary probe has nothing to bind to, and no current is produced.

The hybridization assay described in 11B is especially well suited for determining the viability of microorganisms in solution. It is possible to first use a microstructure to determine whether or not certain microorganisms, such as *C. parvum*, are present in the solution being analyzed. Microstructures such, as those described in FIG. 10 are well suited for this initial detection. If this assay comes up positive, indicating that microorganisms are present, the analyte solution may be heat shocked and subsequently introduced to a second microstructure having a hybridization assay like the one in FIG. 11A or FIG. 11B in order to determine whether or not the microorganisms are alive. This type of immunoassays-hybridization assay combination is especially suitable for use in water treatment facilities to detect dangerous microorganisms contaminating water supplies.

FIG. 12 illustrates an array of microcavities. Array 400 consists of several microcavities 408. Electrodes 402 are parallel to one another and contact multiple microcavities. Electrodes 404 are situated similarly to electrodes 402, but are perpendicular to electrodes 402. Electrodes 404 also contact multiple microcavities. Each microcavity may be designed to have a separate assay within it. Array 400 allows several analytes to be tested for simultaneously. Array 400 may also be composed of microstructures having assays for the same analyte. Electrodes are fused together such that each microstructure simultaneously detects the same analyte. Such an array is especially useful when the analyte is present at extremely low concentrations. Those skilled in the art will recognize this array structure as a means of performing an assay having a sampling technique. This exponentially increases the accuracy of the assay.

Figure 12B:
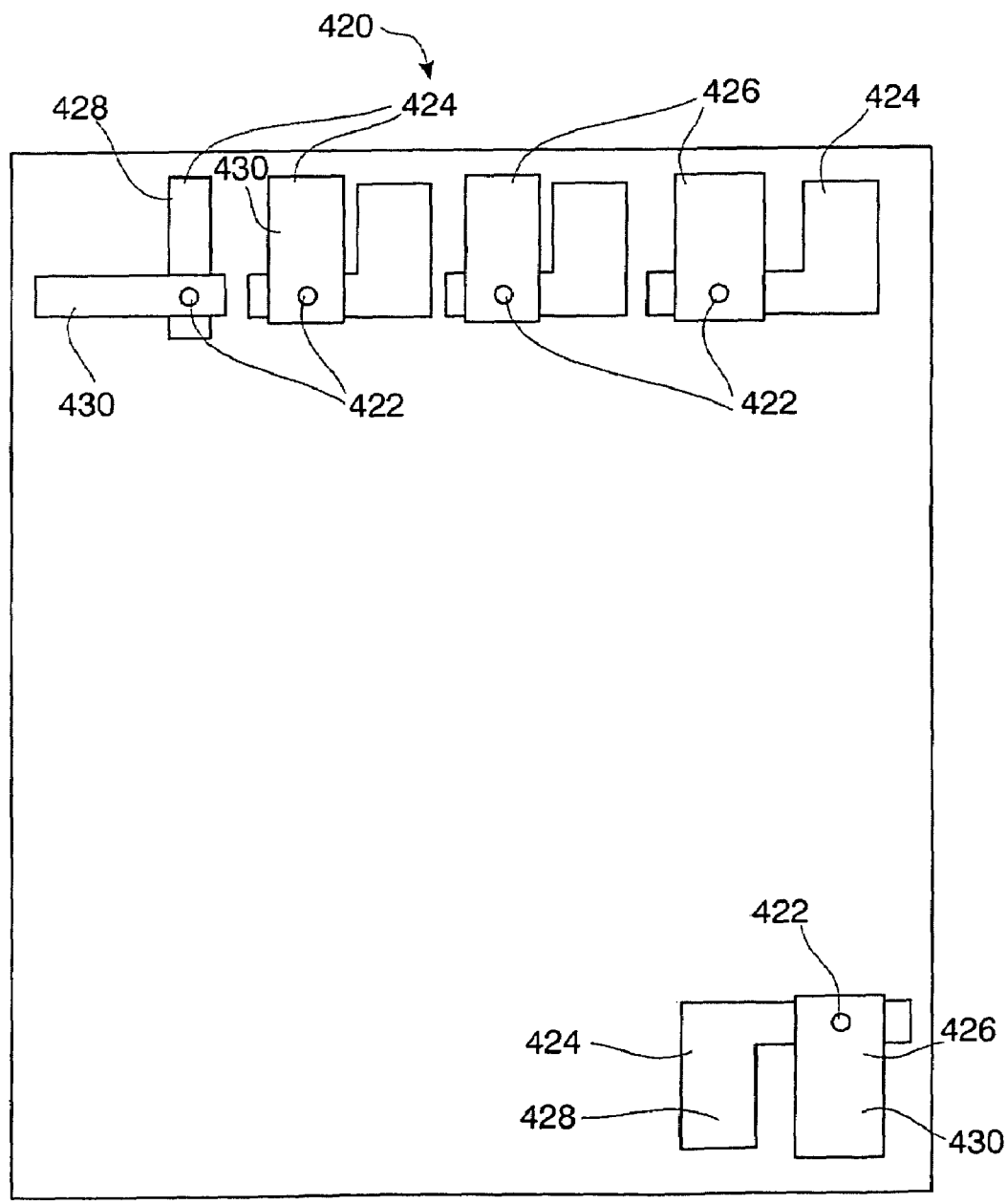
FIG. 12B shows a schematic diagram of an array of independently addressable microcavities.

FIG. 12B shows a partial array 420 individually addressable microcavities 422. In this particular embodiment, bottom electrode 424 serves as a recessed micro disk electrode on the bottom of microcavities 422. Bottom electrodes 424 have contact pads 428 that allow each of them to be addressed individually. Upper electrode 426 forms a thin nanoband electrode within the microcavity. Upper electrodes 426 have contact pads 430 that allow them to be individually addressable. For simplicity, array 420 only shows relatively few microcavities. Additionally, insulating layers and a top conducting layer are not shown either. An array such as the one shown in FIG. 12B is especially useful for facilities desiring to test for pathogens in drinking water and other liquids. Such an array allows for the fabrication of many microcavities having the same microassay within them. Because they are individually addressable, the microstructures may be utilized one at a time. This would allow a single array of individually addressable microstructures to be used many times before it is discarded. In addition, it is a relatively simple matter to short the cavities together so that they may be used simultaneously in order to improve the accuracy of the microassay. Such an array may be utilized to detect the presence of various pathogens. Upon detection, pathogens may be heat shocked and hybridization assays as described in 11A and 11B may be utilized to test for heat shocked polynucleotides. Those skilled in the art will appreciate that, especially on larger scales, it may be desirable to utilize a polymerase chain reaction (PCR) to increase the amount of heat shock polynucleotides present in the sample with micro-scale assays and samples having high concentrations of pathogens, (PCR) is not always necessary. Those skilled in the art will appreciate that the addition of a PCR step to an assay design to detect the presence of and then viability of pathogens as a relatively simple matter.

For reasons of costs and simplicity of manufacture, it may be desirable to utilize assay structures larger than the microstructures described above. Low temperature co-fired ceramics (LTCC) are inexpensive and easily manufactured. Gold ink conducting layers are readily pattered onto LTCC chips. Channels, troughs, wells and pores are all readily machined onto LTCC chips (as well as the microstructures described above) using whole punching or other techniques. The LTCC chips are then layered and co-fired together to form a single chip having several layers. The ceramic assay structures created are generally from 100 micrometers to 1 millimeter in diameter. Although larger than the microstructures described above, they may be formed easily and quickly. The relatively low cost of LTCC chips make them preferable to microstructures in many instances.

The combination of electrochemical assays with microstructures is also uniquely well suited for measuring membrane transport and diffusion. A film or lipid bilayer may be formed over the entrance into the microstructure. Referring to FIGS. 1 and 2, a film may be laid across the top of layer 42. Alternatively, lipids having organothiol groups may be attached to layer 42 in order to begin "anchor" a lipid bilayer membrane across the top of the microcavity.

Upon formation of a film or membrane, the microstructure may then be exposed to any of a number of ions, both metal ions and charged organic molecules. When these ions traverse the film or membrane, they will generate a charge within the microstructure that can be measured. In this way, diffusion across membranes may be measured accurately. The present invention provides a superior method of measuring ion diffusion across various membranes. Other methods of measuring diffusion across membranes involve either electrodes that are a substantial distance from the membrane or electrodes that are actually attached to the membrane. Because the electrode in the present invention is only a few micrometers from the membrane, highly accurate membrane diffusion and transport measurements are possible. When electrodes are attached to the membrane themselves, this covalent attachment draws into question the accuracy of such measurements. It is unknown how attachment of the electrode to the membranes truly affects these diffusion measurements. Those skilled in the art will appreciate that the present invention is a vastly superior device for measuring ion diffusion and transport.

In the case of a lipid bilayer across a microstructure, it is also possible to incorporate membrane transport proteins into the lipid bilayer, thereby facilitating measurement of membrane transport by any of a variety of ion transporting proteins. Currently, the most accurate way of measuring protein transport is by measuring degradation of ATP into ADP. This was primarily accomplished using ATP having $P^{32}$ incorporated as the tertiary phosphorus. Those skilled in the art will appreciate that the method of the present invention is a much safer method of measuring transport. Furthermore, this method obviously only applies to ion transport proteins that are ATPase's. Passive transport proteins may not be measured by this method. Furthermore, measuring ion transport by ATPase's activity is often inaccurate due to the presence of other non-ion transporting ATPase's in the membranes, such as Flippase's. Those skilled in the art will appreciate that the present invention prevents such interference in measurements.

EXAMPLE 1

Fabrication of macrochips. Au macrochips (approximately 1.4 cm×2 cm, where the electroactive area is about 0.6 to 1 $cm_2$) were made from a 125 mm diameter silicon wafer substrate that had 1.4 to 1.8 m $S_iO_2$ deposited on both sides at 250° C. by plasma enhanced chemical vapor deposition (PE-VCD, Plasma Therm System VII). Deposition of a 15 μM adhesion layer of Cr and 1000 μm of Au was carried out using an Edwards Auto 306 TURBO thermal evaporator (Edwards High Vacuum Instrument International, West Sussex, UK). The Au macrochips were diced to size by hand using a diamond scribe. Polyimide (PI) macrochips were made using the Au macrochips as the starting substrate and spin coating a 4 μm thick layer of polyimide followed by cross-linking with UV light at 350 nm for 12 s and curing at 150° C. for 30 min and at 250° C. for another 30 min. The Au coated silicon wafer was spin-rinsed-dried (SRD) using ST 270D (Semitool, Calif.) for a total of 400 s before spin coating the PI. This process completely covers the Au so that the metal does not influence subsequent surface-modification experiments.

Fabrication of microcavity devices. Devices containing functional 50-μm microcavities were fabricated where three patterned layers of Au (with corresponding Cr adhesion layers) are separated from each other by layers of PI on $S_iO_2$-coated silicon wafers. The microcavities are formed by reactive ion etching through these layers, which exposes a RMD electrode at the bottom (50 μm in diameter and 8 μm deep), a TNB electrode along the wall of the microcavity (~500 μm wide and 157 μm long) and a top layer of gold at the rim. The microcavities were cleaned by sonicating (L&R PC3 Compact High Performance Ultrasonic Cleaning System) in acetone or water followed by rinsing with DI water. The chips were then dried with $N_2$ gas and stored in DI water until needed. In an electrochemical study, electrode fouling in the microcavity can be eliminated by sonicating for 30 s in acetone or DI water and minimized by keeping the microcavity in a vial of DI water when not in use.

Macrochip studies to passivate the polyimide insulator. The extent of physisorption of active immunoassays components on PI was studied on PI-coated Au, macrochips. Studies to eliminate physisorption involved pre-testing PI macrochips with different chemical species. The PI macrochips were then carried through all of the same steps of the immunoassays assembly both with or without SAMs of MUA or MUOL as those used to modify the Au macrochips (see assembly steps below). The activity of the modified PI surfaces to convert $PAP_p$ to $PAP_R$ was evaluated by electrochemical detection of the $PAP_R$ in the solution surrounding the PI surface.

Pretreatment of PI macrochips involved exposing the chips to the one of the following solutions overnight: acetate TBSA, acetate TBSA then rinsed three times in DI water followed by exposure to 1.2 mM EDC for 10 min and exposure to 4 mM butanol overnight, acetate TBSA then rinsed three times in DI water followed by exposure to 1.2 mM EDC for 10 min and exposure to 4 mM propionic acid overnight, acetate TBSA then rinsed three times in DI water followed by exposure to 1.2 mM EDC for 10 min and exposure to 4 mM butanol with 4 mM propionic acid overnight, 4 mM 1-mercaptohexane, 4 mM diphenylamine (DPA), 4 mM MOD, 4 mM MOD in acetate TBSA, and 4 mM DPA in acetate TBSA. The 4 mM butanol, 4 mM DPA, 4 mM mercaptohexane, and 4 mM MOD were prepared in ethanol that was purged with Ar. The 4 mM propionic acid solution was prepared with DI water. The PI macro chips were separately soaked overnight in each of the different solutions. The macro chips dipped in solutions prepared in ethanol solvents were first rinsed three times with ethanol. Afterwards, all the chips were rinsed three times in DI water before exposure to subsequent solutions.

Microcavity pretreatment to passivate PI surfaces and electrode cleaning. The best approach for passivating immunoactivity on PI involved pretreatment with 4 mM MOD in acetate TBSA in an Ar-filled glovebag before assembling the immunoassays components. This pretreatment also passivates the gold surfaces of the microcavity device. Passivation was performed by exposing bare microcavity devices to 5 mL acetate TBSA with 4 mM MOD overnight. These were rinsed three times with acetate TBSA and dried with Ar. The passivating films on the RMD (before immunoassays components were assembled) and on the TNB and top layer gold (after immunoassays components were assembled) were removed by electrochemically cycling between +1.5 V to −0.5 V in electrolyte solution of 1 mM $C_aCl_2$ in 0.1 M KCl for at least 30 min at 30 V/s. An alternative procedure involved holding the potential at +0.7 V or −0.5 V in 1 mM $C_aCl_2$ in 0.1 M KCl solution for at least 30 min. Extent of electrode cleanliness and passivation was determined by CV in a solution of 4 mM $K_3F_e(CN)_6$, 1 mM $C_aCl_2$, and 0.1 M KCl.

After electrochemical desorption, the microcavities were cleaned by rinsing with DI water. The chips were dried with $N_2$ gas and stored in DI water until needed. The modified chips are refrigerated in acetate TBSA.

Determination of immunoassays activity on the silicon wafer. To determine whether physisorption to silicon occurs during the macrochip immunoassays, silicon wafer pieces (approximately 1.4 cm×2 cm, without Au or PI) were subjected to the same surface modification processes used for the Au macrochips. The activity of the modified silicon wafer macrochips to convert $PAP_p$ to $PAP_r$ was evaluated by electrochemical detection.

Self-assembled monolayers. The Au macrochips were cleaned in piranha solution (30:70 (v/v) of 30% $H_2O_2$ and concentrated $H_2SO_4$) for 30 min and thoroughly rinsed for 30 min with running DI water before use. SAM preparation, rinsing, and drying were carried out completely in an Ar-purged glovebag after the cleaning step to eliminate oxidation of SAMs by air (or ozone). The Au macrochips were soaked in solutions of either 4 mM MUA or 4 mM MUOL in Ar-purged ethanol for 24 h to form SAMs, followed by rinsing with Ar-purged ethanol three times in each of three separate test tubes inside the glovebag. The chips were dried with Ar and kept in closed vials before use. The same procedure was followed for the formation of SAMs on surfaces of the microcavity, with the exception that the microcavity devices were cleaned by sonication in ethanol for 30 s, instead of piranha solution.

Immobilization of the primary antibody. A working solution of 24 g/mL Ab and 1.2 mM EDC in PB was prepared by combining appropriate volumes of stock solutions of 1.3 mg/mL Ab and 2.4 M EDC in PB, followed by dilution with PB buffer. All of the following steps for antibody immobilization were performed inside a glove bag filled with Ar. SAM-modified macrochips and microcavity devices (which were pre-tested with acetate TBSA and MOD, and for which passivation had been electrochemically removed from the RMD) were soaked in the Ab/EDC working solution for 2 h (1 mL for the macrochip and 200 mL for the microcavity inside a water-saturated, parafilm-sealed petri plate). The EDC assists covalent attachment of the Ab to the free end of the SAMs 43, 59, 60 The chips were rinsed with 1 M NaCl three times and then soaked three times in acetate TBSA (1 mL for the macrochip for 15 min and 50 mL for the microcavity for 30 s, each time) to eliminate non-specifically adsorbed Ab.

Capture of antigen, mouse IgG. Working solutions of the Ag were prepared by dilution of an 11.2 mg/ml Ag stock solution in 0.01 M sodium phosphate buffer in 0.5 M NaCl (pH 8.0) with acetate TBSA. Ab-immobilized macrochips were exposed to a 1 mL solution of 100 ng/mL Ag for 1 h and then rinsed three times with 1 mL of acetate TBSA for 15 min. The Ab-immobilized microcavities were exposed to varying concentrations of Ag ranging from 5 ng/mL to 100 ng/mL by leaving a 1 mL drop of the solution on top of the microcavity for 10 min in a water vapor-saturated petri dish sealed with parafilm (to minimize evaporation). A 1 μL drop in this humid environment does not show any significant evaporation after 66 h at room temperature in the laboratory. The microcavity was rinsed with 50 mL of acetate TBSA three times at 10 s each. These steps were performed outside of the glovebag.

Completing the immunoassay assembly with AP–Ab. A working solution of 700 ng/mL AP–Ab was prepared by diluting a 0.7 mg/mL AP–Ab stock solution in 0.01 M Tris-HCl in 0.25 M NaCl (pH 8.0) with acetate TBSA. Ab-immobilized macrochips that had been exposed to Ag and rinsed, were subsequently exposed to 1 mL of the AP–Ab working solution for 3 h and then rinsed by soaking three times in 5 mL of acetate TBSA for 15 min each to eliminate non-specifically adsorbed AP–Ab. Ab-immobilized microcavity devices that had been exposed to Ag and rinsed, were exposed to 1 L of the AP–Ab working solution for 10 min while inside a parafilm sealed water vapor-saturated petri dish and then rinsed three times with 50 L acetate TBSA for 10 s each. These steps were performed outside of the glovebag.

After deposition of the SAMs with the complete assembly (Ab+Ag+AP–Ab) on the microcavity devices, the passivation layers of the top layer Au and TNB were removed using the same procedures that were used for the removal of the passivation at the RMD. The cleaned TNB and the top layer Au could then be used as working and combination pseudoreference/auxiliary electrodes, respectively.

Enzymatic generation of $PAP_r$. The enzyme substrate solution was 4 mM $PAP_p$ in 0.1 M Tris at pH 9.0, as previously described. The solution was purged with Ar and kept from light to minimize oxidation. Macrochips, containing the complete immunoassay assembly, were rinsed three times with 5 mL 0.1 M Tris at pH 9.0 at 10 min each before soaking in 5 mL of Ar-purged (15-30 minutes) $PAP_p$ solution inside a sealed beaker wrapped in aluminum foil for 24 h inside a glove bag filled with Ar. Microcavity devices, containing the complete assembly and electrochemically-cleaned TNB and top layer electrodes, were rinsed three times with 10 L Tris for 10 s and dried with Ar. The drop size of $PAP_p$ solution placed over the microcavity (inside an Ar-filled glovebag) was 200 nL, and the time for enzymatic conversion varied from 30 s to 2 min. The exact volumes and times for specific experiments are described in the text.

Surface characterization. The various stages of surface modification on Au macrochips were studied using polarization-modulation Fourier transform infrared reflectance absorption spectroscopy (PM-FTIR) with a Mattson Instruments Research Series 1 instrument. The IR beam was focused onto the sample at an incident angle of 77°. The beam was p-polarized and passed through a ZnSe Series II photoelastic modulator (Hinds) operating at 37 kHz before reaching the cooled HgCdTe detector. Spectra were taken with 4 $cm^{-1}$ resolution and a half-wavenumber of 2900 $cm^{-1}$. PM- FTIR spectra were normalized by fitting the differential reflectance spectrum between 4000 cm$^{-1}$ and 2100 cm$^{-1}$ and between 2500 cm$^{-1}$ and 800 cm$^{-1}$ to 3rd order polynomial backgrounds using FitIT curve fitting software (Mattson). After curve fitting, the spectra were truncated and converted to absorbance using a WinFirst macro, written in-house under the specifications of Mattson. The sample chamber was purged with dry CO$^2$-free air from Balston air dryer (Balston, Inc., Haverhill, Mass.). Each modified chip was kept in a vial filled with Ar prior to PM-FTIR analysis.

Electrochemical measurements. A BAS-100B potentiostat and a PA-1 preamplifier with BAS-100W electrochemical software (Bioanalytical Systems, Lafayette, Ind.) were used to perform CV. A Low Current Module and Faraday cage were used for electrochemical experiments on all microcavity devices. All electrochemical experiments involving a small drop of solution on the microcavity involved placing both the device and drop in a petri plate containing water droplets and cotton tips soaked in water to minimize evaporation. Two additional open petri plates containing water were placed inside the Faraday cage to keep the air humid.

Initial electrochemical characterization of all electrodes was performed in a solution containing 4 mM K$_3$F$_e$(CN)$_6$, 1 mM C$_a$Cl$_2$, and 0.1 M KCl. When the Au macrochips and top layer Au of the microcavity devices were characterized, a Pt flag auxiliary electrode and Ag/AgCl (saturated KCl) reference electrode were used. When the RMD and TNB electrodes of the microcavity devices were characterized, an internal setup was used, where the top layer Au served as a combination auxiliary/pseudoreference electrode.

Immunoassay activity of modified Au and PI macrochips was determined by evaluating the surrounding PAP$_p$ solution electrochemically for the presence of PAP$_r$ using an external setup of a bare Au macrochip working electrode, a Pt flag auxiliary electrode, and a Ag/AgCl (saturated KCl) reference electrode. Working electrode potentials were kept within appropriate ranges to avoid electrochemical conversion of PAP$_p$ into PAP$_r$. The Au underlying the modifying layer was never used to detect the enzymatically-generated PAP$_r$.

In the small volume, self-contained, electrochemical immunoassay studies using the microcavity device, immunoassay activity at the modified RMD was determined by evaluating the 200 nL drop of PAP$_p$ solution electrochemically for the presence of PAP$_r$ using an internal setup, where the TNB served as the working electrode and the top layer functioned as a combination auxiliary/pseudoreference electrode. The RMD underlying the modifying layer was never used to detect the enzymatically-generated PAP$_r$.

Modification and characterization of gold macrosubstrates. Studies using SAMs of MUA and MUOL for immobilization of protein and DNA have been previously reported. However, to our knowledge, this is the first report of using MUA and MUOL SAMs for immobilization of rat-anti mouse IgG to gold surfaces in a sandwich-type ELISA for detection of mouse IgG. Consequently, we performed several characterization and activity studies of the modified surfaces. Previously reported studies have used thioctic acid and cysteamine for immobilization of anti human IgE on piezoelectric quartz crystal with gold electrodes. Thioctic acid SAMs have been used for the detection of mouse IgG1 and rabbit IgG. Butanethiol SAMs have been used for rabbit IgG detection. Photoimmobilization of mouse IgG on Au has been accomplished using SAMs of 10,10'-dithiobis(decanoic acid N-hydroxysuccinimide ester) terminated alkyl disulfide. Previous studies have used various SAMs to attach proteins other than IgG.

Each stage of modification (SAM, Ab, Ag, and AP–Ab) exhibited a corresponding increase in absorption in the vibrational modes of both the C—H stretching ( ) region 90-93 (CH3 as 2960 cm-1, CH3 sy 2870 cm-1, CH2 as 2920 cm-1, CH2, sy 2855 cm-1) and the amide region (C═O amide I at 1675 cm-1, N—H amide II at 1545 cm-1, and C—N amide III at 1445 cm-1 where ìasî is asymmetric and ìsyî is symmetric.

Figure 13:
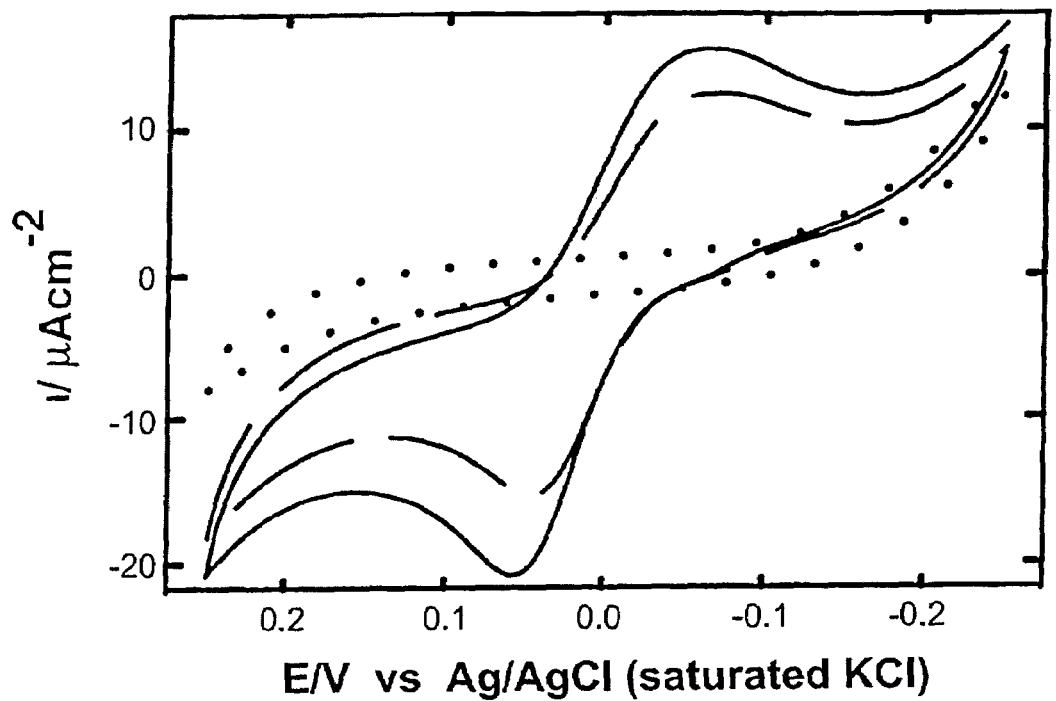
FIG. 13. Demonstration of the necessity of SAMs in the activity of the immunoassay components. CV responses at 25 mV/s using an external setup in 5 ml of 4 mM $PAP_p$ in 0.1 M Tris buffer, after the modified Au macrochip had been soaked in the solution for 24 h. Only Au macrochips containing the complete assembly (Ab+Ag+AP–Ab) with SAMs resulted in a signal that indicated formation of $PAP_R$; MUOL+complete assembly (solid curve), MUA+complete assembly (dashed curve), and complete assembly without SAMs (dotted curve)

Immunoactivity of modified surfaces and the role of self-assembled monolayers was investigated by detecting the enzymatically-generated PAP$_R$ at a nearby bare electrode. The solid and dashed curves in FIG. 13 show typical CV responses using an external electrode setup in a solution of 4 mM PAP$_p$ and 0.1 M Tris, in which a modified Au macrochip surface (SAM+complete assembly) had been soaked for 24 h. Higher currents were obtained when the SAM component of the modified surface was prepared with MUOL than with MUA.

When immunoactivity was investigated at bare Au macrochips that had been exposed to all of the steps in the complete assembly but without the SAM component, no PAP$_R$ was detected. The CV response is shown in FIG. 13 (dotted curve). Nevertheless, PM-FTIR shows significant amounts of physisorption of the individual components of the immunoassay to the Au macrochip in the absence of the SAMs (data not shown). These results suggest that the SAMs are necessary to maintain the active conformations of the immunoassay components on the gold. In addition, physisorption, if any, to the silicon dioxide on the back side of the chip must not contribute to the generation of PAP$_R$. In fact, silicon wafer macrochips that were subjected to the same surface modification steps as Au-coated macrochips showed no electrochemical activity. The specific activity at SAM sites is a useful phenomenon, because it can be used to facilitate the construction of arrays of multi-analyte microassays.

Elimination of physisorption of active species on polyimide. Before transferring the surface modification procedure established for the Au macrochip to the RMD of the microcavity, the adsorption of immunoassay components to polyimide was studied. Polyimide forms the 4 μm thick insulator between metal layers and essentially serves as the main material along the walls of each microcavity. Because the desired immunoassay configuration involves a selectively-modified RMD using electrochemistry to control the site of modification, it would be counterproductive if immunoassay components were to physisorb uncontrollably in their active forms to the surrounding walls.

Polyimide-coated Au macrochips were subjected to the same surface modification processes as the Au macrochips. Note that no Au is exposed on the PI coated chips so that chemistry is confined to the PI on one side of the substrate and silicon dioxide on the other side. The macrochips were then placed in a PAP$_p$ solution for 24 h and CV was obtained at a gold electrode in an external setup arrangement to detect PAP$_R$. The complete assembly with and without the MUOL or MUA exhibited significant generation of PAP$_R$, thereby, indicating that the immunoassay components physisorbed in an active form on the polyimide.

Several strategies were investigated to eliminate the activity on the PI. One approach involved first exposing the PI to acetate TBSA solution in order to block possible protein adsorption sites before proceeding with the immunoassay assembly decreases in the PAP$_R$ current. Assuming the residual activity to be caused by covalent attachment of the Ab to —NH$_2$, —OH, and —COOH functional groups of amino acids of BSA, steps were taken to protect these sites covalently by subsequently exposing substrates to EDC and butanol and propionic acid. This resulted in further decrease but not total elimination of the $PAP_R$ signal. Thus, it seems that PI may have multiple sites of physisorption, which have different affinities for different proteins, or that the size of BSA might prevent complete coverage of those sites.

The second approach to passivate PI activity toward the immunoassay components involved attempts to form more hydrophobic sites on the PI, which should change the nature of the protein adsorption. Thus, the PI was exposed to small molecules of a more hydrophobic nature (MH, MOD, and DPA). Pretreatment of the PI macrochips with DPA, MH, MOD, and a mixture of MH and MOD in ethanol showed a 50% decrease in signal but did not completely eliminate the activity of the immunoassay A combination of acetate TBSA with 4 mM MOD completely passivated the PI. At present we do not know why this process provides successful elimination of the immunoactivity and the others do not. The acetate TBSA+MOD pretreatment was chosen for use with microcavity devices to prevent physisorption of active immunocomponents on the PI.

Electrochemical removal of passivating layers at gold surfaces. Not only does soaking the microcavity devices in acetate TBSA with 4 mM. MOD passivate the PI, but it also passivates the RMD, TNB, and top layer Au. This is an advantage, because it essentially protects the electrode surfaces from fouling during the immunoassay assembly process. Electrochemical desorption, was performed to remove passivation specifically at the RMD. CV in $F_e(CN)_{63-}$ solution, demonstrates that passivation at the RMD is removed but not at the TNB and the top layer gold. The clean RMD was then subjected to the procedure for assembling the SAMs and the immunocomponents (Ab+Ag+AP–Ab).

Only after deposition of the MUOL or MUA SAMs with the complete assembly at the RMD were the passivating layers on the top layer Au and the TNB removed using electrochemical desorption. The cleaned TNB and the top layer Au could then serve as working and pseudoreference/auxiliary electrodes, respectively, to detect $PAP_R$, enzymatically-generated at the modified RMD upon addition of $PAP_p$ solution to the microcavity.

Figure 14:
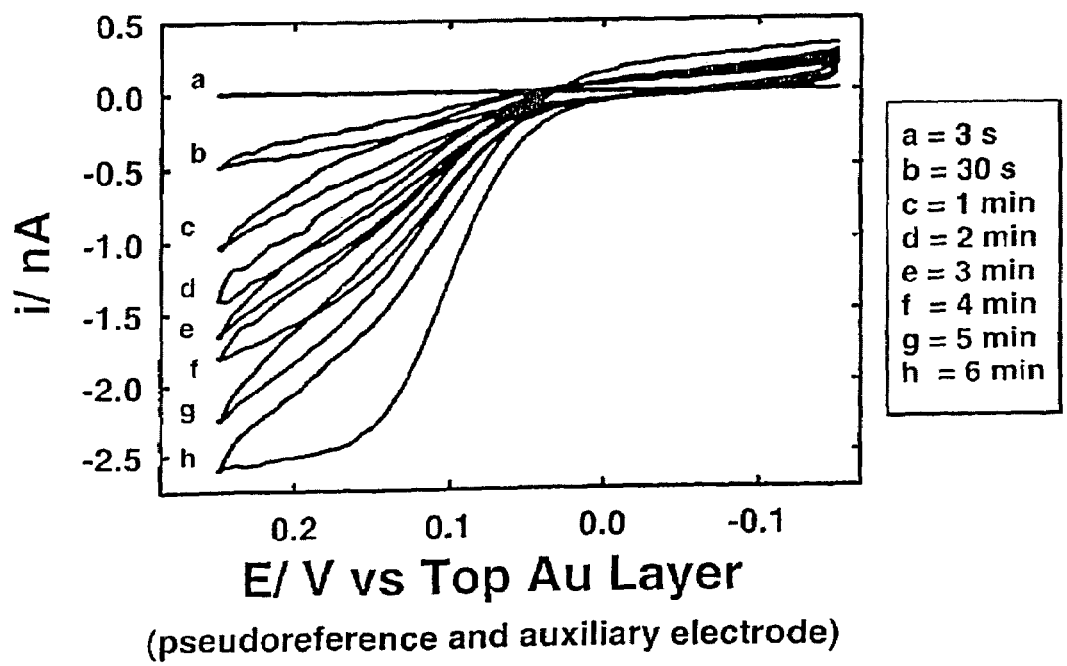
FIG. 14. Timed CV responses at 50 mV/s using a 200 nL drop of 4 mM $PAP_p$ in 0.1 M Tris buffer at a self-contained microelectrochemical immunosensor containing MUOL+ complete assembly with 100 ng/ml mouse IgG. About five seconds after the drop of 4 mM $PAP_p$ was placed on top of the microcavity, CV was performed, which provided the initial response. A second response was obtained after 30 s from the time the drop was placed on top of the modified cavity that indicated a significant increase from the initial response. Subsequent responses were taken at 30 s intervals up to 6 min. (For clarity, not all data are shown.)

Site-specific, self-contained, small volume microelectrochemical immunoassay in a microcavity. In a 50-μm diameter microcavity where steps had been taken to eliminate the physisorption at the PI, the surface of the RMD was modified with MUOL+Ab+Ag+AP-Ab (see FIG. 4), and the top layer of Au and the TNB were electrochemically cleaned. The TNB served as the working electrode and the top layer Au served as the pseudoreference/auxiliary electrode. The volumes of solutions containing Ag and AP–Ab that were used during the assembly were 1 μL. For comparison, the smallest sample volume (which is not allowed to dry) for electrochemical ELISAs reported in the literature and commercially available for mouse IgG is 10 μL. Thus, our sample volume exhibits at least a 10 fold improvement. CV responses at increasing time increments to a 200 nL drop of the $PAP_p$ solution that was placed on top of the modified microcavity are shown in FIG. 14. The volumes of $PAP_p$ solution previously reported in the literature are 20 μL or larger. Hence, our system has accomplished enzyme substrate volume reduction by two orders of magnitude. Even smaller volumes with our system are possible (16 pL for the 50-μm diameter cavity and 0.6 pL for the 10-μm diameter cavity), because working and auxiliary/reference electrodes are located within the microcavity. But because of complications with small sample manipulations and evaporation issues, we only report sample volumes of 200 nL here. Future work will address the smaller volumes.

At only 30 s after the drop of $PAP_p$ solution was placed on top of the modified microcavity, a measurable current of the enzymatically-generated $PAP_R$ was recorded at a scan rate of 50 mV/s (FIG. 14). This quick, measurable response is due to the short distance between the closely spaced working electrode and modified surface (resulting in steep concentration gradients) and to the geometry ($PAP_R$ can only escape from the microcavity by passing by the TNB, although collection efficiency is not 100%). This is a significant improvement over the prior art (excluding SECM), which require incubating the modified electrode in $PAP_p$ or $PNP_p$ for 5 to 30 min before performing electrochemical detection. Subsequent responses exhibit increasing plateau currents due to continuous enzymatic generation of $PAP_R$. Because detection of $PAP_R$ in our system occurs almost immediately after placing the drop on the microcavity, the fraction of $PAP_R$ that is present from non-enzymatic hydrolysis, which could add an unknown background signal that increases exponentially at times beyond 20 min, 47 is minimal. The self-contained microelectrochemical immunoassay experiments also eliminate the need for transfer of solutions because enzymatic generation and detection are carried out in the same space. The total assay time, starting with the addition of Ag solution to the modified cavity and ending when $PAP_R$ is detected, (excluding the electrode-cleaning steps) is 24 min. For comparison, commercial ELISA for mouse IgG has a total assay time (over the same steps) of 1.5-3 h.

Figure 15:
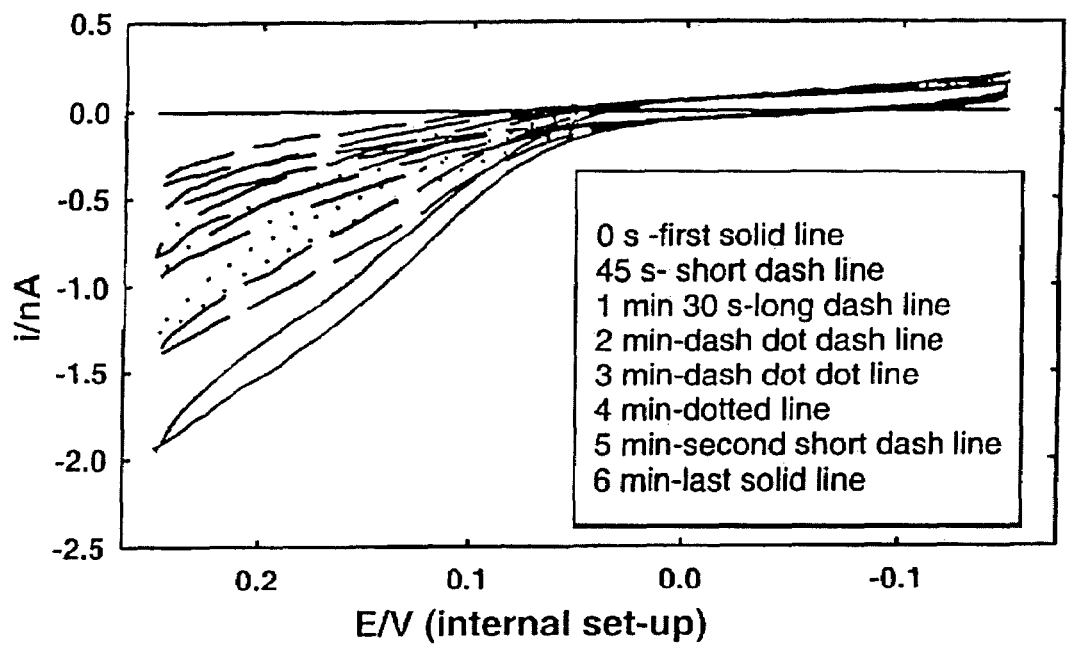
FIG. 15. Timed CV responses using a 0.5 L drop of 4 mM $PAP_p$ (in Tris buffer) from a self-contained microelectrochemical immunosensor containing MUOL+complete assembly with 100 ng/ml mouse IgG at 50 mV/s. About five seconds after the drop of 4 mM $PAP_p$ was placed on top of the microcavity, a current reading was recorded at a scan rate of 50 mV/s that served as the initial response. A second response was recorded after 45 s that indicated a significant increase from the initial response. Subsequent responses were taken at 30 s intervals up to 6 min.

Using a microcavity with surface modification containing MUOL+Ab+Ag+AP–Ab at the RMD, the TNB as working electrode and the top layer Au as the reference and counter electrodes, the timed CV response to 0.5 L (and 0.2 L, not shown) of 4 mM $PAP_p$ placed on top of the modified microcavity is illustrated in FIG. 15. The volume of $PAP_p$ reported in previous literature was 20 L or higher. Hence, our system has accomplished enzyme substrate volume reduction by two orders of magnitude.

About five seconds after the drop of 4 mM $PAP_p$ was placed on top of the microcavity, a current reading was recorded at a scan rate of 50 mV/s that served as the initial response. A second response was recorded after 45 s that indicated a significant increase from the initial response. Subsequent responses are shown in FIG. 15. Previous studies have reported incubating the modified electrode in $PAP_p$ or $PNP_p$ for 5 to 30 min before performing the potential scan. Our system allows performance of the potential scan right after the drop is placed on the microcavity. This eliminates the generation of $PAP_R$ from non-enzymatic hydrolysis that adds an unknown background signal that increases exponentially at times beyond 20 min.

The data in FIG. 15 indicates that the self-contained electrochemistry inside the microcavity has been harnessed to eliminate the need for an external reference and counter electrode in an electrochemical immunoassay. At the same time, the biological component of the immunoassay is contained at the bottom of the same cavity, thereby eliminating the need to transfer the solution as previously reported.

Figure 16:
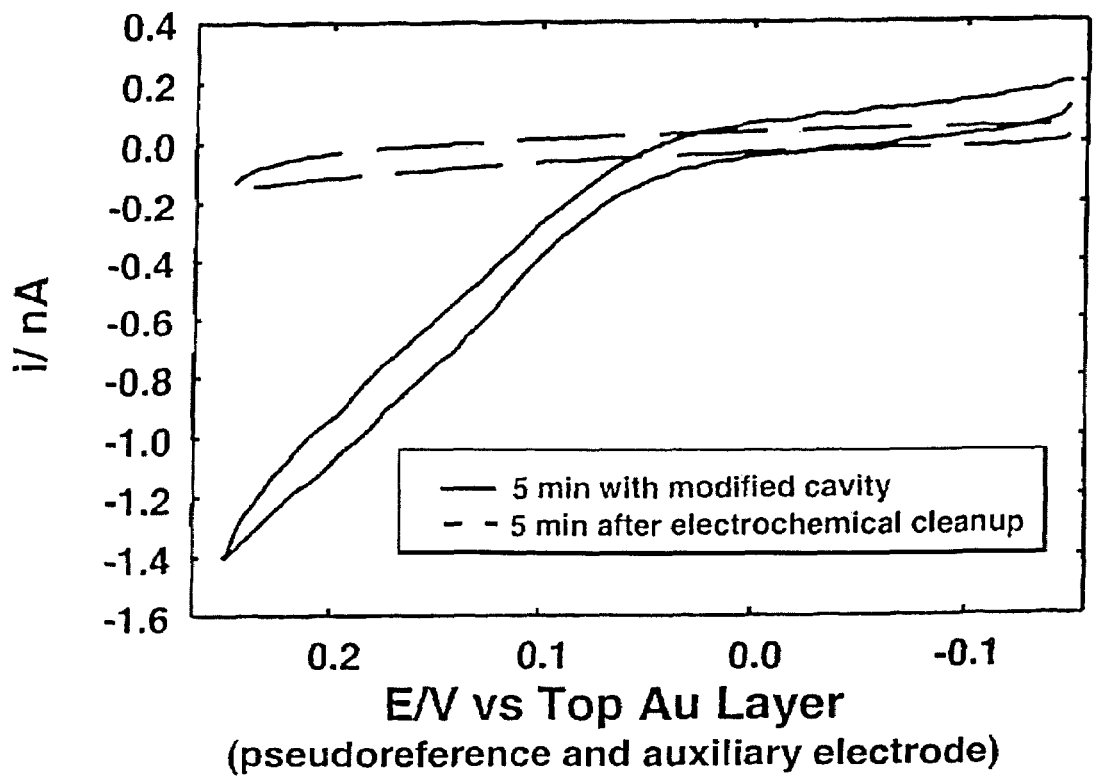
FIG. 16. Demonstration that immunoactivity occurs only at the modified disk in the microcavity and that polyimide-passivation is successful. CV responses are of a self-contained microelectrochemical immunosensor (50 ng/mL IgG) after 5 min in 500 nL 4 mM $PAP_p$ IN 0.1 M Tris, pH 9.0, before (solid line) and after (dashed line) electrochemical removal of the modifying layer (MUOL+Ab+Ag+AP+Ab) at the RMD (50 mV/s, TNB=working, top layer Au=auxiliary/reference)

To determine if modification at the RMD was the only site of immunoactivity in the microcavity, the RMD of an active microelectrochemical immunosensor was subjected to selective electrochemical cleaning to remove the adsorbed substances. The results before and after removal of immunoassay components at the RMD are shown in FIG. 16, and confirm that immunoactivity is absent from the polyimide walls, the TNB, and the top layer of gold. This demonstrates that the PI passivation chemistry is successful, and that subsequent surface chemistry can localize the immunoactivity of these devices.

Figure 17:
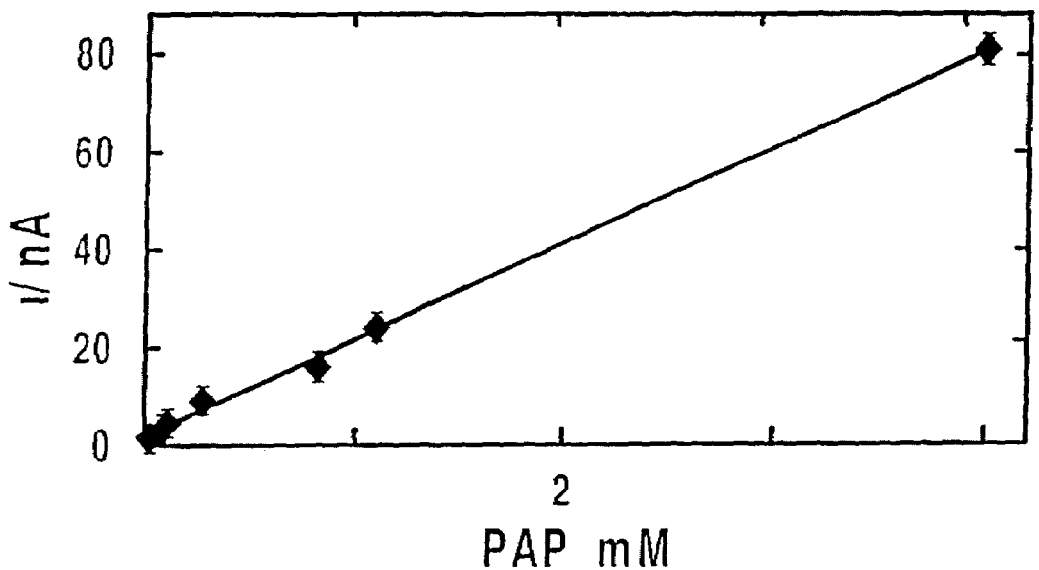
FIG. 17. The sensitivity of the microcavity toward detection of $PAP_R$ was evaluated by establishing a calibration curve. CV at 50 mV/s was carried out on $PAP_R$ solutions (200 nL each) of different concentrations ranging from 5.00 mM to 3.98 mM that were placed top of the 50 m cavity. The calibration curve, which plots the plateau current for the average of two sets of experiments for each concentration of $PAP_R$ gave a linear curve with a $PAP_R$ detection limit of 4.4 nM or 880 fmol. (TNB=working, top layer Au=auxiliary/reference)

Sensitivity and detection limits of the microelectrochemical immunoassay. The performance of a microcavity for detection of $PAP_R$ was evaluated via a calibration curve. This was done by monitoring the CV responses after placing a 200 nL drop of $PAP_R$ solution of different concentrations ranging from 5.00 mM to 3.98 mM directly on a 50-μm diameter cavity. The current (average of two measurements) is linear with concentration and is shown in FIG. 17. A detection limit of 4.4 nM or 880 fmol (or 128 pg) was calculated using the typical equations at the 99%+ confidence level (t is ~3 and there are 16 degrees of freedom), where the slope from the calibration curve is 19.7 0.8 nA/mM, and the standard deviation from the blank signal (17 measurements) from a 200 nL drop of 0.1 M Tris is 29×10-6 nA.

The predicted slope for the calibration curve at the TNB in $PAP_R$ solutions is 8.5 nA/mM, based on the analytic expression for the theoretical diffusion-limited current at an in-plane band electrode at all times (when either radial, planar, or both forms of diffusion contribute). The value of time used in this calculation is the time it takes to sweep from the E1/2 value to the potential at which the current was measured on the reducing side of E1/2. The diffusion coefficient of PAP used is 0.79×10-5 cm2s-1.99. The equation may be adapted to the tubular band geometry in an infinitely long tube as long as the diameter-to-electrode width ratio exceeds 100. The average current for a 4 mM solution from the two sets of experiments used to obtain the calibration curve for $PAP_R$ in FIG. 17 is 80.9 nA, which is much larger than the theoretical value, 34 nA. This may be due to a larger TNB electrode area than expected (some undercutting may occur during the etching process), and access to redox species in a larger volume of solution once the diffusion layer exceeds the confines of the microcavity, and redox equilibrium with bulk solution species through the top metal layer. Current did vary from device to device and from one fabrication batch to another. For example, on average across many devices (n=12), the CV plateau current for a 4 mM $PAP_R$ solution is 54 nA with a standard deviation of 18 nA.

Figure 18:
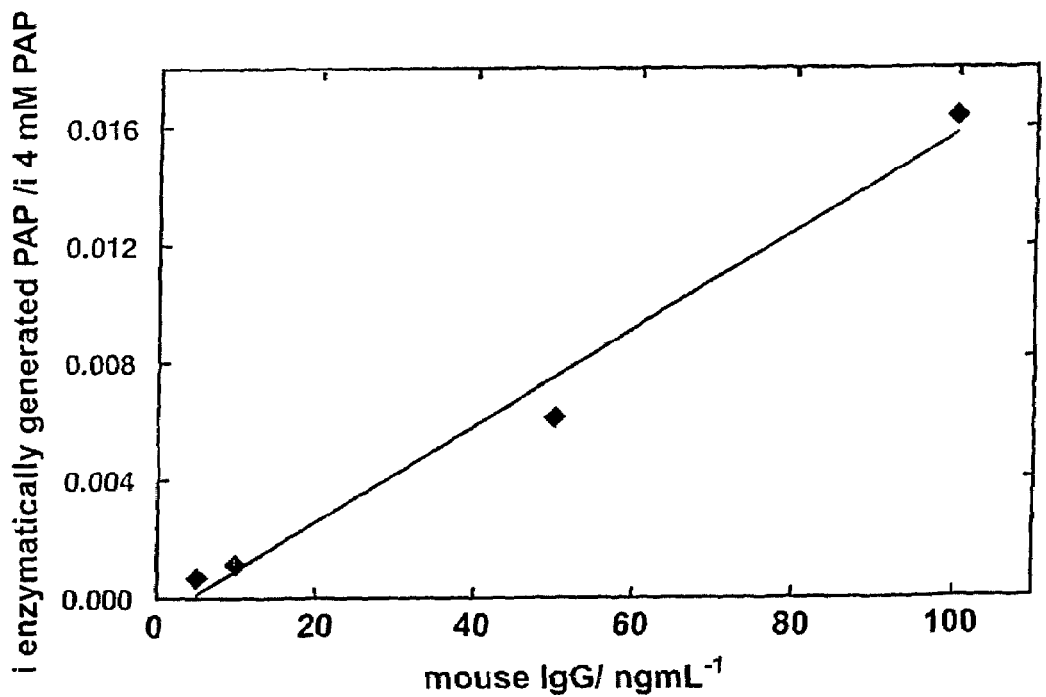
FIG. 18. Calibration curve for mouse IgG concentrations ranging from 5 to 100 ng/ml with a detection limit of 56 zmol. The current readings (after 2 min in 200 nL of 4 mM $PAP_p$ in 0.1 M Tris, pH 9.0) were divided by the current signal from 200 nL of 4 mM $PAP_R$ in 0.1 M Tris pH 9.0, (50 mV/s, TNB=working, top layer Au=auxiliary/reference) using each cavity prior to modification.

The low detection limit that was obtained in studies of $PAP_R$ solutions at a bare microcavity suggest that low detection limits of IgG at modified microcavities may be possible from the enzymatically-generated $PAP_R$. A calibration curve for mouse IgG (FIG. 18) was obtained from CV responses (50 mV s-1) to $PAP_r$ generated after 2 min in a 200 nL drop of 4 mM $PAP_p$ in 0.1 M Tris (pH 9.0) at two different microelectrochemical immunosensors for each of four different concentrations of IgG (5, 10, 50, and 100 ng/ml). Each immunosensor was prepared using a 1 mL drop of IgG solution. Because a different microcavity was involved for each concentration, it was necessary to normalize the immunosensor response. The enzymatically-generated response at each modified microcavity in 4 mM $PAP_p$ solution was divided by the response under similar conditions at the bare microcavity (before modification) in 4 mM $PAP_R$. The resulting number represents the normalized signal, which should be less than or equal to one. A least squares line through the points in the calibration curve produces a slope of 0.165±0.007 mL/ng. The detection limit, using the slope from this line, was determined to be 56 fM (9 pg/mL) or 9 fg (56 zmol) of mouse IgG on a 1 μL drop.

The effect of evaporation vs. enzymatic generation. The concentration of species in the small volumes used throughout the immunoassay studies will change significantly due to evaporation of solvent if precautions are not taken. All steps involving small drops were performed in a sealed, water-saturated environment, with the exception of those involving the $PAP_p$ drop and electrochemical analysis. In the latter case, evaporation still plays a role to some extent, because the humid environment was not completely sealed due to an opening that accommodated the edge connector leads. In order to identify the time limit within which electrochemical analysis on 200 nL $PAP_p$ solutions should be completed, studies on the effect of evaporation were performed.

Because current is proportional to the localized concentration at the detecting electrode, the plateau current of the CV responses of a solution containing a redox species can be used to follow the concentrating effect. The CV plateau current for $PAP_R$ changes with time at a modified microcavity and at a bare microcavity. That for the bare microcavity is constant for about 3 min. After 3 min, and especially noticeable at 5 min, the current rises, presumably due to the concentrating effect of evaporation. There is also a noticeable increase after 3 min, and especially at 5 min for the enzymatically-generated $PAP_R$ at the modified microcavity. Consequently, the increase in current in the first 3 min at the modified microcavity must be due to the turnover of $PAP_p$ to $PAP_R$ by the enzyme and not due to evaporation of water. Therefore, times less than 3 min should be selected when using 200 nL volumes under our conditions, so that determination of detection limit and sensitivity is accurate. The 200 nL drops evaluated at 2 min should be well inside this evaporation limit. Larger drops should show slower concentrating effects due to evaporation.

The $PAP_R$ concentration builds up near the detecting electrode. The CV response obtained in the 4 mM $PAP_R$ solution at the bare microcavity is that which would be expected if all of the 4 mM $PAP_p$ solution were converted to $PAP_R$ by the immobilized alkaline phosphatase at the modified microcavity. After 3 min, the current at the modified microcavity is about 2.15% of that of the bare microcavity based on the signal generated by two chips modified with 100 ng/mL Ag. This leads us to believe that even smaller volumes of $PAP_p$, assuming evaporation is not an issue, should provide even faster increases in signal due to $PAP_R$ production, because the loss due to diffusion outside the microcavity is minimized.

Studies on the effect of evaporation were performed on 0.5 L solution of $PAP_R$ in a humid environment. The CV signal changes with time at a modified microcavity and at a bare microcavity. That for the bare microcavity is constant over about 5 min. After 5 min, the current begins to rise, presumably due to concentration of the $PAP_R$. The percent rise in current after 5 min at the modified microcavity and the bare microcavity are the same. Consequently, the increase in current in the first 5 min at the modified microcavity must be due to the turnover of $PAP_p$ to $PAP_R$ by the enzyme and not due to evaporation of water. Therefore, results for detection limit and sensitivity at small volumes at microcavity devices for times near 5 min or less are not influenced significantly by evaporation.

The $PAP_R$ concentration builds up near the detecting electrode. After only 5 min, about ⅒ of the total concentration of $PAP_p$ can be detected in the form of $PAP_R$, providing a significant signal. Smaller volumes of $PAP_p$ should provide even faster increases in signal due to $PAP_R$ production, because the loss due to diffusion outside the microcavity is minimized.

EXAMPLE 2

The following novel technique was designed because there is no existing electrochemical immunoassay for *Cryptosporidium parvum*-ZPA. Although the method described below is macroscale, those skilled in the art will recognize that it may easily be scaled down to operate within a microstructure as shown in FIG. 10 and may be adapted for detection of a variety of microorganisms simply by changing the antibodies used.

1) Deposit 50 Å(angstrom) chromium (Cr) followed by 1000 Å gold (Au) on 5 on oxidized silicon wafers using thermal vapor deposition.

2) Using a diamond scribe cut the wafer into 1.2×1.2 cm² Au chips.

3) Clean with piranha (3 parts 30% $H_2O_2$ hydrogen peroxide: 7 parts concentrated $H_2SO_4$ sulfuric acid) and rinse thoroughly with running dI water.

4) Deposit self assembled monolayers (SAMs) using 25 mL of 4 mM MUA (mercaptoundecanoic acid) or MUOL (mercaptoundecanol) in ethanol overnight inside an Ar (argon) purged glove bag.

5) Rinse thoroughly with ethanol. Rinse with deionized (dI) water.

6) Soak in 1 mL of 48 mg/mL *Cryptosporidium parvum* Ab (IgM) dissolved in PBS (phosphate buffered saline), pH 6.0 containing 0.1 M EDC (1-ethyl-3-[3-(dimethylaminopropyl)]-carbodiimide hydrochloride) for at least 2 h. Rinse two times with 1 M NaCl (sodium chloride) followed by 0.02 PBS, pH 7.4 3×. Rinse with deionized water.

7) Soak in 1 mL PBS-BSA-GS (phosphate buffered saline-bovine serum albumin-goat serum) overnight inside the refrigerator.

8) Outside the glovebag soak in 1 mL *Cryptosporidium* oocysts (previously heat shocked at 43° C. for 10 minutes) diluted with the 0.02 PBS-BSA-GS, pH 7.4 to desired concentration from a stock of $10^6$ oocyts/4 mL for 6 h. Rinse with PBS-BSA-GS 3×. Rinse two times with acetate TBSA (tween bovine serum albumin), pH 5.0. Rinse with dI water.

9) Soak in 1 mL alkaline phosphatase labeled antibody to *Cryptosporidium parvum* oocysts (10 mL of synthesized Ab−AP in 1 mL 0.02 PBS-BSA-GS) for 4 h. Rinse 3× with PBS-BSA-GS. Rinse with acetate TBSA 2×. Rinse with dI water.

10) Inside the glovebag, soak in 5 mL of Ar purged 4 mM para-aminophenyl phosphate (PAPP) in 0.1 M Tris, pH 9.0 inside a capped beaker wrapped in Al foil overnight (ON) inside an Ar purged glovebag.

11) Remove the modified chip, Ar purge the PAPP for 20 to 30 min then run a cyclic voltammetry (CV) using a clean Au macro chip as working electrode (WE), Ag/AgCl in saturated KCl as reference and platinum (Pt) flag as counter electrodes.

PBS-BSA-GS: 0.02 M PBS (phosphate buffered saline), pH 7.4 with 1% Bovine serum albumin, 10% goat serum, and 0.02% sodium azide.

EXAMPLE 3

The novel DNA-hybridization Assay for *Cryptosporidium parvum*-Macro system described below was developed to demonstrate the feasibility of the viability assay for microorganisms. Those skilled in the art will appreciate that this method is easily scaled down to work inside a microstructure, as shown in FIG. 11B.

Make sure all solutions and solvents are filtered with 0.2 μm filter. Vortex all solutions before to use. Autoclave deionized (dI) water for all solutions. Use only RNAse and DNAase free reagents without autoclaving.

Macro Chips

1) Deposit ~100 Å Cr/1000 Å Au on 5 in silicon wafer ($Si/SiO_2$) using BOC Edwards Thermal Evaporator.

2) Dice with a diamond tip scrib to 1.2×1.2 $cm^2$ pieces or macro chips.

3) Soak macro chips in piranha solution for 30 min then wash thoroughly with running dI water.

MUOL SAMs

1) Inside an AR filled glovebag, soak the chips in 4 mM MUOL in ethanol overnight.

2) Rinse three times with ethanol followed by dI water.

DNA Probe 1 ($P_1$)

1) Place the MUOL modified macro chip in a solution containing 5 mL solution of Probe 1 in 1 mL of 0.2 M EDC in 0.1 M PBS, pH 6.0.

2) Incubate at room temperature (RT) or 41° C. for 0.5 to 3 h.

3) Rinse 3× in 2×SSC (sodium chloride sodium citrate buffer) using 5 mL each for 5 mm.

4) Rinse with 1×SSC then soak in 20×SSC for at lest 0.5 h.

Hybridization of Target DNA (T)

1) Place 5 mL T in 1 mL 20×SSC.

2) Soak macro chips previously modified with MUOL+P1.

3) Incubate for 0.5 to 3 h at RT or 41° C.

4) Rinse 3 times in 2×SSC using 5 mL each for 5 min.

5) Rinse with 1×SSC then soak in 20×SSC for at lest 0.5 h.

Hybridization of DNA Probe 2 ($P_2$)

1) Add 5 mL $P_2$ in 1 mL 20×SSC.

2) Soak macro chips previously modified with MUOL+$P_1$+T

3) Incubate for 0.5 to 3 h at RT or 41° C.

4) Rinse 3 times in 2×SSC using 5 mL each for 5 min.

5) Rinse with 1×SSC then rinse with filtered 0.1 M Tris, pH 9.0.

Bioassay

1) Soak the SAMs+$P_1$+T+$P_2$−AP modified macro chip in 5 mL of 4 mM PAPP in an Aluminum foil wrapped beaker with a cap overnight in an Ar-saturated glovebag.

2) Using a clean bare Au macro chip as working electrode, platinum flag as counter electrode, and Ag/AgCl (saturated KCl) as reference electrode, perform cyclic voltammetry on the solution surrounding the modified macro chip at 50 $mVs^{-1}$.

Whereas, the present invention has been described in relation to the drawings attached hereto, it should be understood that other and further modifications, apart from those shown or suggested herein, may be made within the spirit and scope of this invention.

What is claimed is:

1. A method for detecting chemical compounds, said method comprising the steps of:

addition of a sample to immunomicrobeads;

allowing an analyte in said sample to bind to an analyte-binding material on a surface of said immunomicrobeads;

rinsing said immunomicrobeads such that said analyte remains bound to said analyte-binding material while the remainder of said sample is removed;

incorporating said immunomicrobeads into a microassay structure, said microassay structure comprising at least one three-dimensional microstructure having a substrate and alternating conducting layers and insulating layers, wherein said conducting layers comprise a plurality of independently addressable electrodes sandwiched between said insulating layers, and wherein said microassay structure includes a material that facilitates physiabsorbtion of said immunomicrobeads;

allowing said analyte-binding material to attach to one of said conducting layers or said insulating layers;

addition of a secondary analyte-binding material having an electroactive complex attached, said electroactive complex having an electroactive species capable of generating an electric current and/or voltage by either accepting or transmitting one or more electrons to at least one of said electrodes;

allowing said secondary analyte-binding material to bind to said analyte;

rinsing said microassay structure such that only said secondary analyte-binding material bound to said analyte remain in said microassay structure;

activating said electroactive complex such that said electroactive species is released from said electroactive complex resulting in said electric current and/or voltage to be generated within said microassay structure, wherein said step of activating of said electroactive complex is selected from the group consisting of change in temperature, change in pH, denaturation or addition of an activating compound; and measuring said electric current and/or voltage within said microassay structure.

2. The method of claim 1 wherein said electroactive complex is selected from the group consisting of proteins, enzymes, metalloproteins, dendrimers, redox enzymes, protein-enzyme conjugate, nucleotide-enzyme conjugate or chelating agents.

3. The method of claim 1 wherein said analyte-binding material is selected from the group consisting of antibodies, polynucleotides, lipid layers, dendrimer or a protein binding compound.

4. The method of claim 1 wherein said analyte-binding material is comprised of antibodies, polynucleotides, lipid layers, ligands, proteins or a protein binding compound covalently bound to a self assembled monolayer or a polymer attached to at least one of said conducting layers or insulating layers.

5. The method of claim 1 wherein said analyte-binding material is specific to said analyte in said sample.

6. The method of claim 1 wherein said secondary analyte-binding material is specific to said analyte bound to said analyte-binding material.

7. The method of claim 1 wherein said analyte-binding material is a plurality of analyte-binding materials and said secondary analyte-binding material is a plurality of secondary analyte-binding materials.

8. The method of claim 7 wherein said plurality of secondary analyte-binding materials are added as a mixture in a single solution or individually in different solutions.

9. The method of claim 7 wherein said electroactive complex is activated individually or as a mixture.

10. The method of claim 7 wherein said electric current and said voltage generated by said electroactive complex are measured in a simultaneous process or as a combined signal.

11. The method of claim 7 wherein said plurality of analyte-binding materials are individually attached to at least one of said conducting layers or said insulating layers of said microstructure.

12. The method of claim 1 wherein said microstructure is a mirocavity.

13. The method of claim 12 wherein said microcavity has an open end and a closed end, such that access to said analyte-binding material is via said open end.

14. The method of claim 1 wherein said insulating layers are non-conductive and separate the conductive layers.

15. The method of claim 1 wherein at least one of said electrodes is a bottom layer of said microstructure.

16. The method of claim 15 wherein said analyte binding material is tethered directly to said electrode on said bottom layer of said microstructure.

17. The method of claim 1 wherein said alternating conducting layers and insulating layers form at least one wall of said microstructure.

18. The method of claim 1 wherein said conducting layers comprise materials selected from the group consisting of metals and inorganic materials.

19. The method of claim 1 wherein said alternating conducting layers and insulating layers are constructed using photolithography, vapor deposition, sputtering or electroplating.

20. The method of claim 1 wherein said microstructure is a micropore.

21. The method of claim 1 wherein said substrate comprises materials selected from the group consisting of a silicon wafer, ceramic, glass and a polymer.

* * * * *